United States Patent
Flynn et al.

(10) Patent No.: US 9,457,019 B2
(45) Date of Patent: Oct. 4, 2016

(54) METHODS FOR INHIBITING TIE-2 KINASE USEFUL IN THE TREATMENT OF CANCER

(71) Applicant: Deciphera Pharmaceuticals, LLC, Lawrence, KS (US)

(72) Inventors: Daniel L. Flynn, Lawrence, KS (US); Michael D. Kaufman, Lawrence, KS (US); Bryan D. Smith, Lawrence, KS (US); Marc Rudoltz, West Orange, NJ (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 0 days.

(21) Appl. No.: 14/535,900

(22) Filed: Nov. 7, 2014

(65) Prior Publication Data

US 2015/0246033 A1 Sep. 3, 2015

Related U.S. Application Data

(60) Provisional application No. 61/901,316, filed on Nov. 7, 2013.

(51) Int. Cl.

| | |
|---|---|
| *A61K 38/00* | (2006.01) |
| *A61K 31/4709* | (2006.01) |
| *C07D 401/14* | (2006.01) |
| *A61K 45/06* | (2006.01) |
| *A61K 31/337* | (2006.01) |
| *A61K 31/351* | (2006.01) |
| *C07K 16/40* | (2006.01) |
| *A61K 31/357* | (2006.01) |

(52) U.S. Cl.
CPC ......... *A61K 31/4709* (2013.01); *A61K 31/337* (2013.01); *A61K 31/351* (2013.01); *A61K 31/357* (2013.01); *A61K 45/06* (2013.01); *C07D 401/14* (2013.01); *C07K 16/40* (2013.01)

(58) Field of Classification Search
None
See application file for complete search history.

(56) References Cited

U.S. PATENT DOCUMENTS

| 7,790,756 B2 * | 9/2010 | Flynn | C07D 401/12 514/341 |
|---|---|---|---|
| 8,586,565 B2 * | 11/2013 | Flynn | C07D 401/12 514/249 |
| 2011/0207752 A1 * | 8/2011 | Geeganage | A61K 31/517 514/262.1 |
| 2015/0290316 A1 * | 10/2015 | Graziano | C07K 16/2803 424/174.1 |

FOREIGN PATENT DOCUMENTS

| WO | 2008/156712 | * 12/2008 |
|---|---|---|
| WO | 2013/036232 | * 3/2013 |

OTHER PUBLICATIONS

Nelson et al., Ann. Intern Med. 2009; 151:727-737.*
Kataja et al., Ann Oncol 2009; 20(sup 4): iv10-14.*
Balmana et al. Ann Oncol 2009; 20(supp 4):iv19-20.*
Liu et al, "TIE2/TEK Modulates the Interaction of Glioma and Brain Tumor Stem Cells With Endothelial Cells and Promotes an Invasive Phenotype" Oncotarciet (2010) 1: 700-709.
Brunckhorst et al, "Angiopoietin-4 Promotes Glioblastoma Progression by Enhancing Tumor Cell Viability and Angiogenesis" Cancer Research (2010) 70: 7283-7293.
Helfrich et al, "Angiopoietin-2 Levels Are Associated With Disease Progressino in Metastatic Malignant Melanoma" Clin Cancer Res (2009) 15: 1384-1392.
Karlan et al, "Randomized, Double-Blind, Placebo-Controlled Phase II Study of AMG 386 Combined With Weekly Paclitaxel in Pateitns With Recurrent Ovarian Cancer" J. Clinical Oncology (2012) 30: 362-370.
Ahmad et al, "Differential Expression of Angiopoietin-1 and Angiopoietin-2 in Colon Carcinoma" Cancer (2001) 92: 1138-1143.
Hashizume et al, "Complementary Actions of Inhibitors of Angiopoietin-2 and VEGF on Tumor Angiogenesis and Growth" Cancer Research (2010) 70: 2213-2223.
Matsubara et al,"TIE2-Expressing Monocytes as a Diganostic Marker for Hepatocellular Carcinoma Correlates With Angiogenesis" Hepatology (2013) 57: 1416-1425.
Mitsuhashi et al, "Angiopoietins and TIE-2 Expression in Angiogenesis and Proliferation of Human Hepatocellular Carcinoma" Hepatology (2003) 37: 1105-1113.
Tanaka et al, "Biologic Signaificance of Angiopoietin-2 Expression in Human Hepatocellular Carcinoma" J. Clin Invest (1999) 103: 341-345.
Muller et al, "Expression of Angiopoietin-1 and its Receptor TEK in Hematopietic Cells From Patients With Myeloid Leukemia" Leukemia Research (2002) 26: 163-168.
Hou et al, "Expression of Angiopoietins and Vascular Endothelial Growth Factors and Their Clinical Significance in Acute Myeloid Leukemia" *Leukemia Research* (2008) 32: 904-912.
Peinado et al, "Melanoma Exosomes Educate Bone Marrow Progenitor Cells Toward a Pro-Metastatic Phenotype Through MET" *Nature Medicine* (2012) 18: 883-891.
Schindler et al. "Structural Mechanism for STI-571 Inhibition of Abelson Tyrosine Kinase" Science (2000) 289: 1938-1942.

* cited by examiner

*Primary Examiner* — Sheela J Huff
(74) *Attorney, Agent, or Firm* — Cooley LLP

(57) ABSTRACT

The present invention relates to methods of inhibiting TIE2 kinase useful in the treatment of tumor growth, invasiveness, intravazation, dissemination, metastasis, and immunosuppression. Specifically, the invention relates to methods of using 1-(3-tert-butyl-1-(quinolin-6-yl)-1H-pyrazol-5-yl)-3-(2-fluoro-4-(2-(methylcarbamoyl)pyridin-4-yloxy)phenyl) urea and salts thereof of Formula I.

42 Claims, 7 Drawing Sheets

METHODS FOR INHIBITING TIE-2 KINASE USEFUL IN THE TREATMENT OF CANCER

CROSS-REFERENCE TO RELATED APPLICATION

This application claims the benefit of U.S. Provisional Patent Application No. 61/901,316, filed Nov. 7, 2013, entitled "METHODS FOR INHIBITING TIE-2 KINASE USEFUL IN THE TREATMENT OF CANCER," which is incorporated herein by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DECP_066_01US_SeqList_ST25.txt, date recorded: Nov. 7, 2014, file size 6 kilobytes).

FIELD OF THE INVENTION

The present invention relates to methods of inhibiting TIE2 kinase useful in the treatment of tumor growth, tumor invasiveness, tumor intravasation, tumor dissemination, tumor metastasis, and tumor immunotolerance. Specifically, the invention relates to methods of using compositions of Formula I herein described as potent inhibitors of TIE2 for treating breast cancer growth, invasiveness, intravasation dissemination, metastasis, and immunotolerance.

BACKGROUND OF THE INVENTION

Tunica interna endothelial cell kinase-2 (TIE2) is largely restricted to expression in endothelial cells of the vasculature, and in a subset of bone marrow derived TIE2 expressing monocytes (TEMs). TIE2 is the receptor for angiopoietin 1 (ANG1), angiopoietin 2 (ANG2), and angiopoietin 4 (ANG4) and this signaling system plays an important role in both angiogenesis (sprouting of new vessels from existing vessels) and vasculogenesis (de novo new vessel formation). TEMs are a subset of circulating monocytes and tissue macrophages that have proangiogenic and provasculogenic activity in tumor models (De Palma M D et al, *Cancer Cell* 2005; 8:211-226). TIE2 inhibition decreases the ability of TEMs to associate with blood vessels (Mazzieri R, *Cancer Cell* 2011; 19:512-526) and markedly decreases the proangiogenic activity of this macrophage subset (De Palma M, *Clin Cancer Res* 2011; 17(16):5226-5232).

Cytotoxic chemotherapy, radiation therapy, and anti-angiogenic treatments damage the tumor-associated vasculature thus leading to a hypoxic tumor environment. The hypoxic tumor environment leads to rebound tumor vascularization by activating an angiogenic switch from the vascular endothelial growth factor (VEGF)/VEGFR2 pathway to the ANG/TIE2 pathway in vascular endothelial cells. The recruitment of pro-vasculogenic TEMs from the bone marrow to these hypoxic tumor sites facilitates this revascularization by the association of TEMs with endothelial cells within the tumor microenvironment. TEMs and TIE2-expressing endothelial cells are thus believed to play an important role in the revascularization of tumors after these treatments, leading to progression due to the growth of residual tumor cells (De Palma M, et al. *Trends Immunol* 2007; 28:519-524).

TIE2 is also a mediator of osteoclast differentiation, and TIE2 inhibition led to decreased osteolytic bone invasion and decreased tumor growth in the 4T1 mouse breast cancer model (Dales J P, et al. *Int J Oncol* 2003; 22:391-397). Beyond the physiologic expression of TIE2 on endothelial, monocyte/macrophage, and osteoclast cells of the tumor microenvironment, TIE2 has also been demonstrated to be present on breast cancer cells. Tumor cell expression of TIE2 was associated with an elevated risk of metastatic disease and an independent predictor of prognosis on multivariate analysis (Min Y, et al. *Cancer Res* 2010; 70:2918-2828).

Significantly, a subset of TIE2-expressing tissue macrophages are located within specialized vascular structures known as tumor microenvironment for metastases (TMEMs). Recent observations have linked TIE2-expressing macrophages within TMEM structures as being essential for extravasation of breast cancer cells into the vascular circulation and subsequent dissemination to distal metastatic sites (Condeelis J, Pollard J W. *Cell* 2006; 124:263-6; Ginter P S, et al. *Cancer Res* 2012; 72(24 Suppl):Abstract #P6-02-04). Thus inhibition of TIE2, and of the macrophages within TMEM structures, may lead to a decrease in new metastases.

TIE2-expressing tissue macrophages (TEMs) have recently been demonstrated to play a role in breast cancer immunotolerance. TEMs from breast tumors are able to suppress tumor-specific immune responses. Specifically, suppressive functions of TEMs are similarly driven by TIE2 and VEGFR kinase activity. TEMs isolated from breast cancer tissue can function as antigen-presenting cells that elicit only a weak proliferation of T cells. Blocking TIE2 and VEGFR kinase activity induced TEMs to change their phenotype into cells with features of myeloid dendritic cells with robust antigen-presentation. Immunosuppressive activity of TEMs is also associated with high CD86 surface expression and extensive engagement of T regulatory cells in breast tumors. TIE2 and VEGFR kinase activities were required to maintain high CD86 surface expression levels and to convert T cells into immunosuppressive regulatory cells (Ibberson M, et al. *Clin Cancer Res* 2013; 19:3439-3449).

The polyoma middle-T antigen (PyMT) syngeneic mouse breast cancer model utilizes the mouse mammary tumor virus (MMTV) promoter, a breast specific promoter, to express PyMT in mouse breast tissue. In this model, PyMT breast cancer cells are implanted in the mouse mammary fat pad, and these cancers metastasize and lead to the death of the mouse. Unlike xenograft models, the PyMT model utilizes fully immunocompetent mice. Metastasis in this model is known to be modulated by TIE2 expressing macrophages within TMEM vascular structures. Thus, there is a need for new treatments for diseases associated with TIE2.

SUMMARY OF THE INVENTION

Methods of the present invention find utility in the inhibition TIE2 kinase. As a result of this inhibition the present invention is useful in the treatment or prophylaxis against of tumor growth, invasiveness, intravasation, dissemination, metastasis, and tumor immunotolerance. In particular, the invention relates to methods of using compositions of Formula I, described below, as potent inhibitors of TIE2 for treating breast cancer growth, invasiveness, intravasation, dissemination, metastasis, and immunotolerance:

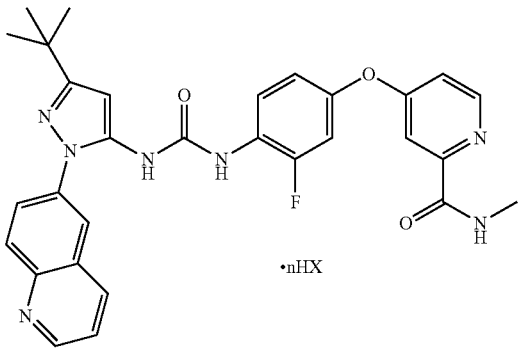

Formula I wherein
n is an integer from 0 to 7;
X is the basic radical of a pharmaceutically acceptable salt;
provided that when n is 0, the composition of Formula I is the parent free base. In some embodiments, HX is absent whereby the structure of Formula I is the parent free base.

The compositions of Formula I also find utility in other cancers wherein TIE2 expression, either in the tumor cell or in the tumor microenvironment, causes tumor progression by mechanisms mediating primary tumor growth, primary tumor invasiveness, tumor intravasation into the blood stream, tumor cell dissemination, tumor metastases to distal tissues, or tumor immunotolerance Inhibition of TIE2 kinase by the composition of Formula I therefore finds utility in the treatment of cancer by inhibiting processes including primary tumor growth, primary tumor invasiveness, tumor intravasation into the blood stream, tumor cell dissemination, tumor metastases to distal tissues, or tumor immunotolerance.

TIE2 kinase has been shown to be causative of cancer progression in gliomas (Liu et al, *Oncotarget* (2010) 1: 700-709; Brunckhorst et al, *Cancer Research* (2010) 70: 7283-7293), melanomas (Helfrich et al, *Clin Cancer Res* (2009) 15: 1384-1392), ovarian cancer (Karlan et al, *J. Clinical Oncology* (2012) 30: 362-370), colorectal cancer (Ahmad et al, *Cancer* (2001) 92: 1138-1143; Hashizume et al, *Cancer Research* (2010) 70: 2213-2223), hepatocellular carcinoma (Matsubara et al, *Hepatology* (2013) 57: 1416-1425; Mitsuhashi et al, *Hepatology* (2003) 37: 1105-1113; Tanaka et al, *J. Clin Invest* (1999) 103: 341-345), and hematological cancers (Muller et al, *Leukemia Research* (2002) 26: 163-168; Hou et al, *Leukemia Research* (2008) 32: 904-912).

DETAILED DESCRIPTION OF THE INVENTION

Definitions

Figure 1:
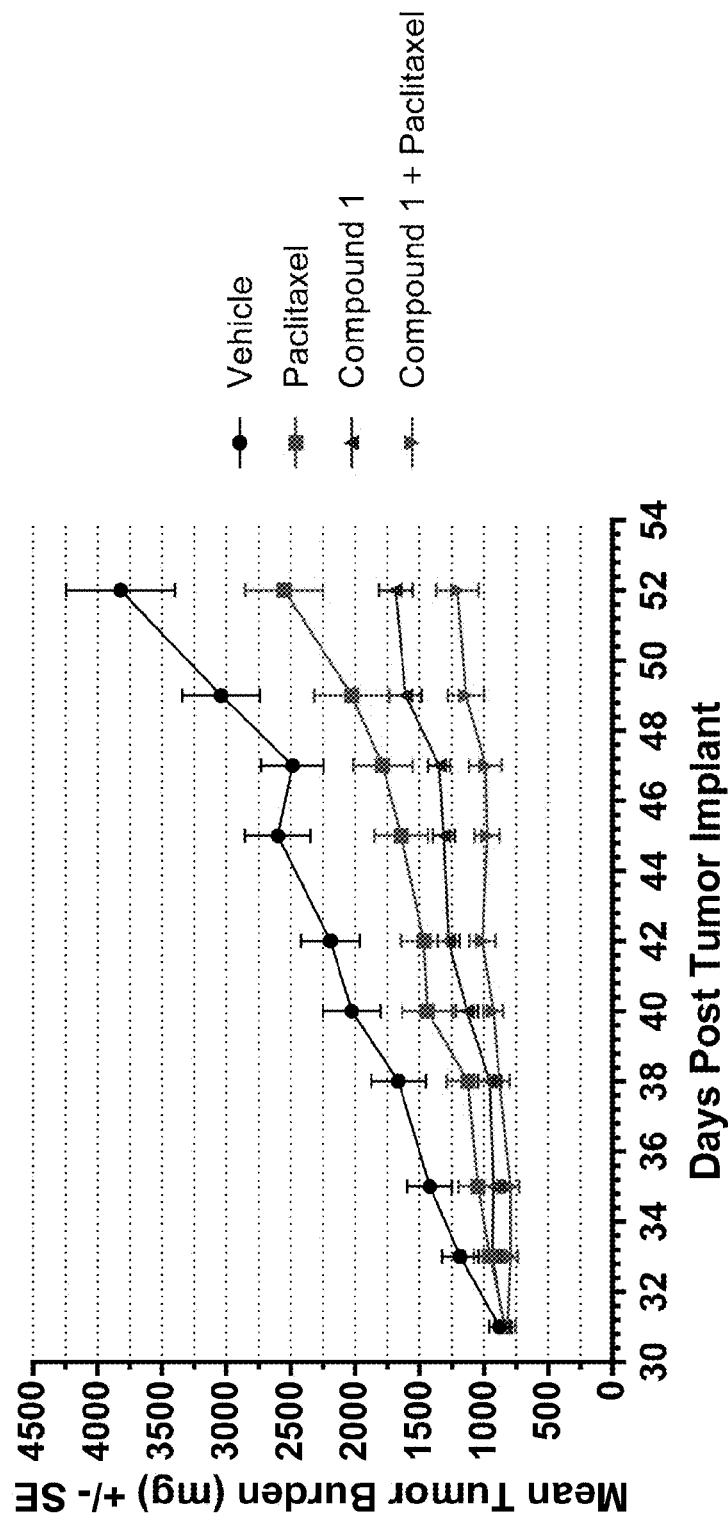
FIG. 1 shows the inhibition of primary PyMT tumor growth using the composition of Formula II, paclitaxel, or a combination thereof.

The term "basic radical of a pharmaceutically acceptable salt" in compositions of Formula I include, without limitation, water-soluble and water-insoluble salts, such as substituted or unsubstituted benzenesulfonate, the acetate, amsonate (4,4-diaminostilbene-2,2-disulfonate), benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. Specific examples of the basic radicals include para-toluene sulfonate, triflate, and methanesulfonate.

The term "salt" refers to pharmaceutically acceptable salts
The term "pharmaceutically acceptable salt" also refers to a salt of the compositions of the present invention having an acidic functional group, such as a carboxylic acid functional group, and a base.

The term "treating" with regard to a subject, refers to improving at least one symptom of the subject's disorder. Treating can be curing, improving, or at least partially ameliorating the disorder.

The term "administer", "administering", or "administration" as used in this disclosure refers to either directly administering a composition or pharmaceutically acceptable salt of the compound or a composition to a subject, or administering a prodrug derivative or analog of the composition or pharmaceutically acceptable salt of the compound or composition to the subject, which can form an equivalent amount of active compound within the subject's body.

An "effective amount," when used in connection with medical uses is an amount that is effective for providing a measurable treatment, prevention, or reduction in the rate of pathogenesis of a disease of interest.

The present invention relates to methods of the treatment (blocking) or prophylaxis against tumor growth, invasiveness, intravasation, dissemination, metastasis, and tumor immunotolerance. The method comprises administering to a patient in need of treatment or reduction of prophylactic effects of these conditions an effective amount of a composition of Formula I herein described in a dosing regimen that regulates TIE2 inhibition.

The amount of composition described herein needed for achieving a therapeutic effect may be determined empirically in accordance with conventional procedures for the particular purpose. Generally, for administering therapeutic agents (e.g. compositions of Formulae I or II (and/or additional agents) described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. For example, administration of therapeutic agents to a patient suffering from cancer provides a therapeutic benefit not only when the underlying condition is eradicated or ameliorated, but also when the patient reports a decrease in the severity or duration of the symptoms associated with the disease, e.g., a decrease in tumor burden, a decrease in circulating tumor cells, an increase in progression free survival. Therapeutic benefit also includes halting or slowing the progression of the underlying disease or disorder, regardless of whether improvement is realized.

In one embodiment of the invention, the composition of Formula I is 1-(3-tert-butyl-1-(quinolin-6-yl)-1H-pyrazol-5-yl)-3-(2-fluoro-4-(2-(methylcarbamoyl)pyridin-4-yloxy)phenyl)urea para-toluene sulfonic acid salt of Formula II which is a potent inhibitor of TIE2, the receptor tyrosine kinase for angiopoietin ligands.

Formula II

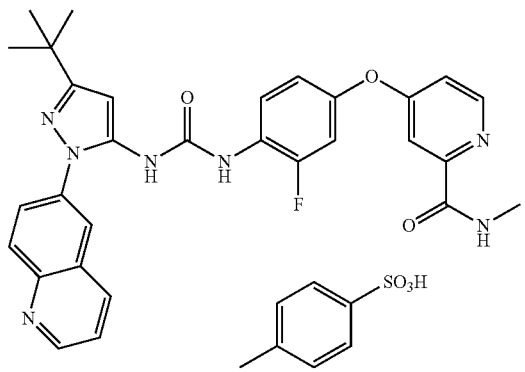

The compositions of Formula I find utility in cancers wherein TIE2 expression, either in the tumor cell or in the tumor microenvironment, causes tumor progression by mechanisms mediating primary tumor growth, primary tumor invasiveness, tumor intravasation into the blood stream, tumor cell dissemination, tumor metastases to distal tissues, or tumor immunotolerance. Inhibition of TIE2 kinase by the composition of Formula I therefore finds utility in the treatment of cancer by inhibiting processes including primary tumor growth, primary tumor invasiveness, tumor intravasation into the blood stream, tumor cell dissemination, tumor metastases to distal tissues, or tumor immunotolerance.

Therapeutic concentrations of the compositions of Formula I block cells within the tumor microenvironment known to cause tumor growth, invasion, intravasation, dissemination, metastases, of tumor induced immunotolerance. Such cell types within the tumor microenvironment include TIE2-expressing monocytes, TIE2-expressing macrophages, and TIE2-expressing endothelial cells.

Tumors responsive to angiopoietin/TIE2 signaling include but are not limited to breast cancer, ovarian cancer, hepatocellular carcinoma, gliomas, colorectal cancer, and hematological malignancies.

In another embodiment, the composition of Formula I when the HX is absent is the free base compound 1-(3-tert-butyl-1-(quinolin-6-yl)-1H-pyrazol-5-yl)-3-(2-fluoro-4-(2-(methylcarbamoyl)pyridin-4-yloxy)phenyl)urea having the structure:

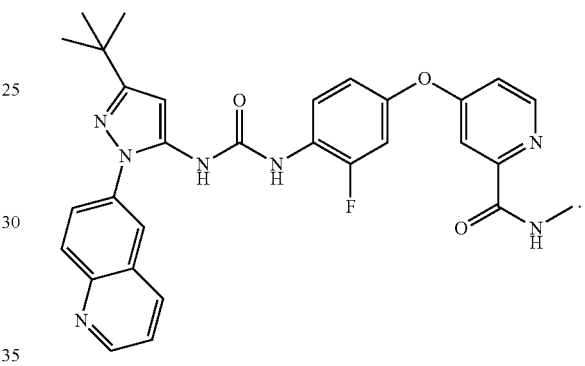

The composition of Formula I may be administered as a single agent or in combination with other therapeutic agents known to treat cancers. Such other therapeutic agents include radiation therapy, anti-tubulin agents, DNA alkylating agents, DNA synthesis-inhibiting agents, DNA intercalating agents, anti-estrogen agents, anti-androgens, steroids, anti-EGFR agents, kinase inhibitors, topoisomerase inhibitors, Histone Deacetylase (HDAC) inhibitors, DNA methylation inhibitors, anti-HER2 agents, anti-angiogenic agents, proteasome inhibitors, thalidomide, lenalidomide, antibody-drug-conjugates (ADCs), immunomodulating agents, or cancer vaccines.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the prophylactic effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

When the compositions of Formulae I or II are used in combination with other anti-cancer agents, the other anti-cancer agent may be dosed independently of the dosing schedule of the composition of Formulae I or II. The other anti-cancer agent may be dosed at its previously established therapeutic dose and dosing schedule, or its dose and dosing schedule may be modified to optimize efficacy, safety or tolerability when used in combination with the compositions of Formulae I or II.

Further, any compositions of Formulae I or II (and/or additional agents) described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

The compositions of Formula I may be used in combination with other agents including chemotherapeutic agents, targeted therapeutics, biological agents, or radiotherapy.

The compositions of Formula I may be used in combination with chemotherapeutic agents including but not limited to anti-tubulin agents (paclitaxel, paclitaxel protein-bound particles for injectable suspension, eribulin, docetaxel, ixabepilone, vincristine), vinorelbine, DNA-alkylating agents (including cisplatin, carboplatin, oxaliplatin, cyclophosphamide, ifosfamide, temozolomide), DNA intercalating agents (including doxorubicin, pegylated liposomal doxorubicin, daunorubicin, idarubicin, and epirubicin), 5-fluorouracil, capecitabine, cytarabine, decitabine, 5-aza cytadine, gemcitabine and methotrexate.

The compositions of Formula I may be used in combination with kinase inhibitors including but not limited to erlotinib, gefitinib, lapatanib, everolimus, temsirolimus, LY2835219, LEE011, PD 0332991, crizotinib, cabozantinib, sunitinib, pazopanib, sorafenib, regorafenib, axitinib, dasatinib, imatinib, nilotinib, vemurafenib, dabrafenib, trametinib, idelalisib, and quizartinib.

The compositions of Formula I may be used in combination with anti-estrogen agents including but not limited to tamoxifen, fulvestrant, anastrozole, letrozole, and exemestane.

The compositions of Formula I may be used in combination with anti-androgen agents including but not limited to abiraterone acetate, enzalutamide, nilutamide, bicalutamide, flutamide, cyproterone acetate.

The compositions of Formula I may be used in combination with steroid agents including but not limited to prednisone and dexamethazone.

The compositions of Formula I may be used in combination with topoisomerase I inhibitors including but not limited to irinotecan, camptothecin, and topotecan.

The compositions of Formula I may be used in combination with topoisomerase II inhibitors including but not limited to etoposide, etoposide phosphate, and mitoxantrone.

The compositions of Formula I may be used in combination with Histone Deacetylase (HDAC) inhibitors including but not limited to vorinostat, romidepsin, panobinostat, valproic acid, and belinostat.

The compositions of Formula I may be used in combination with DNA methylation inhibitors including but not limited to DZNep and 5-aza-2'-deoxycytidine.

The compositions of Formula I may be used in combination with proteasome inhibitors including but not limited to bortezomib and carfilzomib.

The compositions of Formula I may be used in combination with thalidomide, lenalidomide and pomalidomide.

The compositions of Formula I may be used in combination with biological agents including but not limited to trastuzumab, ado-trastuzumab, pertuzumab, cetuximab, panitumumab, ipilimumab, anti-PD-1 agents including labrolizumab and nivolumab, anti-PD-L1 agents including MPDL3280A, anti-angiogenic agents including bevacizumab and aflibercept, and antibody-drug-conjugates (ADCs) including brentuximab vedotin and trastuzumab emtansine.

The compositions of Formula I may be used in combination with radiotherapy.

The compositions of Formula I may be used in combination with therapeutic vaccines including but not limited to sipuleucel-T.

In some embodiments, the composition of Formula I or Formula II can be used in combination with one or more of the other agents described herein.

Methods for Blocking Primary Breast Tumor Growth and Invasiveness:

A first aspect of the invention relates to a method of blocking primary breast tumor growth and invasiveness which comprises administering to a patient in need thereof an effective amount of a composition of Formula I in a dosing regimen sufficient to block TIE2 kinase in the tumor microenvironment.

In one embodiment of this aspect of the invention, the dosing regimen of the composition of Formula I is a daily dosing administration.

In another embodiment of this aspect of the invention the dosing regimen of the composition of Formula I is a daily dosing administration. The intermittent non-daily dosing regimen may include, without limitation, alternate daily dosing, every third-day dosing, twice weekly dosing, or once weekly dosing.

In another embodiment of this aspect of the invention, a suitable dosing regimen of the composition of Formula I includes administration twice weekly, once weekly, or alternate weekly.

In another embodiment of this aspect of the invention, the dosing regimen of the composition of Formula I is twice weekly or once weekly.

In other embodiments of this aspect of the invention, the dosing regimen of the composition of Formula I is administration twice weekly.

In yet another embodiment of the invention, the method of blocking primary breast tumor growth and invasiveness comprises administering a composition of Formula I in a dosing regimen sufficient to block TIE2 kinase in the tumor microenvironment in combination with one or more agents taken from an anti-tubulin agent, a DNA alkylating agent, a DNA synthesis-inhibiting agent, a DNA intercalating agent, an anti-estrogen agent, an anti-HER2 agent, a kinase inhibitor or an anti-angiogenic agent.

In another embodiment of this aspect of the invention, the method of blocking primary breast tumor growth and invasiveness comprises administering a composition of Formula I in combination with paclitaxel.

In another embodiment of this aspect of the invention, the method of blocking primary breast tumor growth and invasiveness comprises administering a composition of Formula I in combination with paclitaxel protein-bound particles for injectable suspension.

In another embodiment of this aspect of the invention, the method of blocking primary breast tumor growth and invasiveness comprises administering a composition of Formula I in combination with docetaxel.

In another embodiment of this aspect of the invention, a method of blocking primary breast tumor growth and invasiveness comprises the administration of a composition of Formula I in combination with eribulin.

In another embodiment of this aspect of the invention, a method of blocking primary breast tumor growth and invasiveness comprises the administration of a composition of Formula I in combination with ixabepilone.

In another embodiment of this aspect of the invention, a method of blocking primary breast tumor growth and invasiveness comprises the administration of a composition of Formula I in combination with vinorelbine.

In another embodiment of this aspect of the invention, the method of blocking primary breast tumor growth and invasiveness comprises the administration of a composition of Formula I in combination with capecitabine.

In another embodiment of this aspect of the invention, the method of blocking primary breast tumor growth and invasiveness comprises the administration of a composition of Formula I in combination with gemcitabine.

In another embodiment of this aspect of the invention, the method of blocking primary breast tumor growth and invasiveness comprises the administration of a composition of Formula I in combination with 5-fluorouracil.

In another embodiment of this aspect of the invention, the method of blocking primary breast tumor growth and invasiveness comprises the administration of a composition of Formula I in combination with methotrexate.

In another embodiment of this aspect of the invention, the method of blocking primary breast tumor growth and invasiveness comprises the administration of a composition of Formula I in combination with cyclophosphamide.

In another embodiment of this aspect of the invention, the method of blocking primary breast tumor growth and invasiveness comprises the administration of a composition of Formula I in combination with cisplatin.

In another embodiment of this aspect of the invention, the method of blocking primary breast tumor growth and invasiveness comprises the administration of a composition of Formula I in combination with carboplatin.

In another embodiment of this aspect of the invention, the method of blocking primary breast tumor growth and invasiveness comprises administering of a composition of Formula I in combination with doxorubicin.

In another embodiment of this aspect of the invention, the method of blocking primary breast tumor growth and invasiveness comprises administering of a composition of Formula I in combination with pegylated liposomal doxorubicin.

In another embodiment of this aspect of the invention, the method of blocking primary breast tumor growth and invasiveness comprises administering of a composition of Formula I in combination with epirubicin.

In yet another embodiment of this aspect of the invention, the method of blocking primary breast tumor growth and invasiveness comprises the administration of a composition of Formula I in combination with tamoxifen.

In another embodiment of this aspect of the invention, the method of blocking primary breast tumor growth and invasiveness comprises the administration of a composition of Formula I in combination with fulvestrant.

In another embodiment of this aspect of the invention, the method of blocking primary breast tumor growth and invasiveness comprises the administration of a composition of Formula I in combination with anastrozole.

In another embodiment of this aspect of the invention, the method of blocking primary breast tumor growth and invasiveness comprises the administration of a composition of Formula I in combination with letrozole.

\In another embodiment of this aspect of the invention, the method of blocking primary breast tumor growth and invasiveness comprises the administration of a composition of Formula I in combination with exemestane.

In another embodiment of this aspect of the invention, the method of blocking primary breast tumor growth and invasiveness comprises the administration of a composition of Formula I in combination with trastuzumab.

In another embodiment of this aspect of the invention, the method of blocking primary breast tumor growth and invasiveness comprises the administration of a composition of Formula I in combination with ado-trastuzumab emtansine.

In another embodiment of this aspect of the invention, the method of blocking primary breast tumor growth and invasiveness comprises administering a composition of Formula I in combination with pertuzumab.

In another embodiment of this aspect of the invention, the method of blocking primary breast tumor growth and invasiveness comprises the administration of a composition of Formula I in combination with lapatinib.

In another embodiment of this aspect of the invention, the method of blocking primary breast tumor growth and invasiveness comprises the administration of a composition of Formula I in combination with everolimus.

In another embodiment of this aspect of the invention, the method of blocking primary breast tumor growth and invasiveness comprises the administration of a composition of Formula I in combination with temsirolimus.

In another embodiment of this aspect of the invention, the method of blocking primary breast tumor growth and invasiveness comprises the administration of a composition of Formula I in combination with the CDK4/6 inhibitor LY2835219.

In another embodiment of this aspect of the invention, the method of blocking primary breast tumor growth and invasiveness comprises the administration of a composition of Formula I in combination with the CDK4/6 inhibitor LEE011.

In another embodiment of this aspect of the invention, the method of blocking primary breast tumor growth and invasiveness comprises the administration of a composition of Formula I in combination with the CDK4/6 inhibitor PD 0332991.

In another embodiment of this aspect of the invention, the method of blocking primary breast tumor growth and invasiveness comprises the administration of a composition of Formula I in combination with bevacizumab.

Another aspect of the invention relates to a method of blocking primary breast tumor growth and invasiveness which comprises the administration of a composition of Formula I at doses sufficient to block TIE2 kinase in the tumor microenvironment, wherein the composition of Formula I is administered in an intermittent non-daily dosing regimen. In some embodiments, the intermittent non-daily dosing regimen, includes alternate daily dosing, every third daily dosing, twice weekly dosing, and once weekly dosing.

In another embodiment of this aspect of the invention, a method of blocking primary breast tumor growth and invasiveness comprises the administration of a composition of Formula I at doses sufficient to block TIE2 kinase in the tumor microenvironment, wherein the composition of Formula I is administered twice weekly, once weekly, or alternate weekly.

In another embodiment of this aspect of the invention, a method of blocking primary breast tumor growth and invasiveness comprises the administration of a composition of Formula I at doses sufficient to block TIE2 kinase in the tumor microenvironment, wherein the composition of Formula I is administered twice weekly or once weekly.

In another embodiment of this aspect of the invention, a method of blocking primary breast tumor growth and invasiveness comprises the administration of a composition of Formula I at doses sufficient to block TIE2 kinase in the tumor microenvironment, wherein the composition of Formula I is administered twice weekly.

In another embodiment of this aspect of the invention, a method of blocking primary breast tumor growth and invasiveness comprises the administration of a composition of Formula I at doses sufficient to block TIE2 kinase in the tumor microenvironment wherein the composition of Formula I is administered in combination with one or more agents taken from an anti-tubulin agent, a DNA alkylating agent, a DNA synthesis-inhibiting agent, a DNA intercalating agent, an anti-estrogen agent, an anti-HER2 agent, a kinase inhibitor or an anti-angiogenic agent.

In another embodiment of this aspect of the invention, the method of blocking primary breast tumor growth and invasiveness comprises administering a composition of Formula I in combination with paclitaxel.

In another embodiment of this aspect of the invention, the method of blocking primary breast tumor growth and invasiveness comprises administering a composition of Formula I in combination with paclitaxel protein-bound particles for injectable suspension.

In another embodiment of this aspect of the invention, the method of blocking primary breast tumor growth and invasiveness comprises administering a composition of Formula I in combination with docetaxel.

In another embodiment of this aspect of the invention, a method of blocking primary breast tumor growth and invasiveness comprises the administration of a composition of Formula I in combination with eribulin.

In another embodiment of this aspect of the invention, a method of blocking primary breast tumor growth and invasiveness comprises the administration of a composition of Formula I in combination with ixabepilone.

In another embodiment of this aspect of the invention, a method of blocking primary breast tumor growth and invasiveness comprises the administration of a composition of Formula I in combination with vinorelbine.

In another embodiment of this aspect of the invention, the method of blocking primary breast tumor growth and invasiveness comprises the administration of a composition of Formula I in combination with capecitabine.

In another embodiment of this aspect of the invention, the method of blocking primary breast tumor growth and invasiveness comprises the administration of a composition of Formula I in combination with gemcitabine.

In another embodiment of this aspect of the invention, the method of blocking primary breast tumor growth and invasiveness comprises the administration of a composition of Formula I in combination with 5-fluorouracil.

In another embodiment of this aspect of the invention, the method of blocking primary breast tumor growth and invasiveness comprises the administration of a composition of Formula I in combination with methotrexate.

In another embodiment of this aspect of the invention, the method of blocking primary breast tumor growth and invasiveness comprises the administration of a composition of Formula I in combination with cyclophosphamide.

In another embodiment of this aspect of the invention, the method of blocking primary breast tumor growth and invasiveness comprises the administration of a composition of Formula I in combination with cisplatin.

In another embodiment of this aspect of the invention, the method of blocking primary breast tumor growth and invasiveness comprises the administration of a composition of Formula I in combination with carboplatin.

In another embodiment of this aspect of the invention, the method of blocking primary breast tumor growth and invasiveness comprises administering of a composition of Formula I in combination with doxorubicin.

In another embodiment of this aspect of the invention, the method of blocking primary breast tumor growth and invasiveness comprises administering of a composition of Formula I in combination with pegylated liposomal doxorubicin.

In another embodiment of this aspect of the invention, the method of blocking primary breast tumor growth and invasiveness comprises administering of a composition of Formula I in combination with epirubicin.

In yet another embodiment of this aspect of the invention, the method of blocking primary breast tumor growth and invasiveness comprises the administration of a composition of Formula I in combination with tamoxifen.

In another embodiment of this aspect of the invention, the method of blocking primary breast tumor growth and invasiveness comprises the administration of a composition of Formula I in combination with fulvestrant.

In another embodiment of this aspect of the invention, the method of blocking primary breast tumor growth and invasiveness comprises the administration of a composition of Formula I in combination with anastrozole.

In another embodiment of this aspect of the invention, the method of blocking primary breast tumor growth and invasiveness comprises the administration of a composition of Formula I in combination with letrozole.

In another embodiment of this aspect of the invention, the method of blocking primary breast tumor growth and invasiveness comprises the administration of a composition of Formula I in combination with exemestane.

In another embodiment of this aspect of the invention, the method of blocking primary breast tumor growth and invasiveness comprises the administration of a composition of Formula I in combination with trastuzumab.

In another embodiment of this aspect of the invention, the method of blocking primary breast tumor growth and invasiveness comprises the administration of a composition of Formula I in combination with ado-trastuzumab emtansine.

In another embodiment of this aspect of the invention, the method of blocking primary breast tumor growth and invasiveness comprises administering a composition of Formula I in combination with pertuzumab.

In another embodiment of this aspect of the invention, the method of blocking primary breast tumor growth and invasiveness comprises the administration of a composition of Formula I at doses sufficient to block TIE2 kinase in tumor microenvironment TIE2-expressing macrophages administered in combination with lapatinib.

In another embodiment of this aspect of the invention, the method of blocking primary breast tumor growth and invasiveness comprises the administration of a composition of Formula I at doses sufficient to block TIE2 kinase in tumor microenvironment TIE2-expressing macrophages administered in combination with everolimus.

In another embodiment of this aspect of the invention, the method of blocking primary breast tumor growth and invasiveness comprises the administration of a composition of Formula I at doses sufficient to block TIE2 kinase in tumor microenvironment TIE2-expressing macrophages administered in combination with temsirolimus.

In another embodiment of this aspect of the invention, the method of blocking primary breast tumor growth and invasiveness comprises the administration of a composition of Formula I at doses sufficient to block TIE2 kinase in tumor microenvironment TIE2-expressing macrophages administered in combination with the CDK4/6 inhibitor LY2835219.

In another embodiment of this aspect of the invention, the method of blocking primary breast tumor growth and invasiveness comprises the administration of a composition of Formula I at doses sufficient to block TIE2 kinase in tumor microenvironment TIE2-expressing macrophages administered in combination with the CDK4/6 inhibitor LEE011.

In another embodiment of this aspect of the invention, the method of blocking primary breast tumor growth and invasiveness comprises the administration of a composition of Formula I at doses sufficient to block TIE2 kinase in tumor microenvironment TIE2-expressing macrophages administered in combination with the CDK4/6 inhibitor PD 0332991.

In another embodiment of this aspect of the invention, the method of blocking primary breast tumor growth and invasiveness comprises the administration of a composition of Formula I in combination with bevacizumab.

Methods for Blocking Breast Cancer Intravasation, Dissemination and Metastasis:

In yet another aspect of the invention a method of blocking breast cancer intravasation, dissemination and metastasis is provided which comprises administering to patient in need thereof an effective amount of a composition of Formula I sufficient to block TIE2 kinase in the tumor microenvironment.

In one embodiment of this aspect of the invention, the method of blocking breast cancer intravasation, dissemination and metastasis comprises administering to patient in need thereof an effective amount of a composition of Formula I in a dosing regimen sufficient to block TIE2 kinase in the tumor microenvironment.

In another embodiment of this aspect of the invention, the dosing regimen sufficient to block breast cancer intravasation, dissemination and metastasis comprises the daily administration of a composition of Formula I.

In another embodiment of this aspect of the invention, the dosing regimen of a composition of Formula I is administered in an intermittent non-daily dosing manner, including alternate daily dosing, every third daily dosing, twice weekly dosing, or once weekly dosing.

In another embodiment of this aspect of the invention, the dosing regimen of a composition of Formula I is administered twice weekly, once weekly, or alternate weekly.

In another embodiment of this aspect of the invention, the dosing regimen of a composition of Formula I is twice weekly or once weekly administration.

In another embodiment of this aspect of the invention, the dosing regimen a composition of Formula I is administered twice weekly.

In another embodiment of this aspect of the invention, the method of blocking breast cancer intravasation, dissemination and metastasis comprises administering to a patient in need thereof an effective amount of a composition of Formula I in a dosing regimen sufficient to block TIE2 kinase in the tumor microenvironment in combination with one or more agents taken from an anti-tubulin agent, a DNA alkylating agent, a DNA synthesis-inhibiting agent, a DNA intercalating agent, an anti-estrogen agent, an anti-HER2 agent, a kinase inhibitor or an anti-angiogenic agent.

In another embodiment of this aspect of the invention, the method of blocking breast cancer intravasation, dissemination and metastasis comprises administering a composition of Formula I in combination with paclitaxel.

In another embodiment of this aspect of the invention, the method of blocking breast cancer intravasation, dissemination and metastasis comprises administering a composition of Formula I in combination with paclitaxel protein-bound particles for injectable suspension.

In another embodiment of this aspect of the invention, the method of blocking breast cancer intravasation, dissemination and metastasis comprises administering a composition of Formula I in combination with docetaxel.

In another embodiment of this aspect of the invention, the method of blocking breast cancer intravasation, dissemination and metastasis comprises administering a composition of Formula I in combination with eribulin.

In another embodiment of this aspect of the invention, the method of blocking breast cancer intravasation, dissemination and metastasis comprises administering a composition of Formula I in combination with ixabepilone.

In another embodiment of this aspect of the invention, the method of blocking breast cancer intravasation, dissemination and metastasis comprises administering a composition of Formula I in combination with vinorelbine.

In another embodiment of this aspect of the invention, the method of blocking breast cancer intravasation, dissemination and metastasis comprises administering a composition of Formula I in combination with capecitabine.

In another embodiment of this aspect of the invention, the method of blocking breast cancer intravasation, dissemination and metastasis comprises administering a composition of Formula I in combination with gemcitabine.

In another embodiment of this aspect of the invention, the method of blocking breast cancer intravasation, dissemination and metastasis comprises administering a composition of Formula I in combination with 5-fluorouracil.

In another embodiment of this aspect of the invention, the method of blocking breast cancer intravasation, dissemination and metastasis comprises administering a composition of Formula I in combination with methotrexate.

In another embodiment of this aspect of the invention, the method of blocking breast cancer intravasation, dissemination and metastasis comprises administering a composition of Formula I in combination with cyclophosphamide.

In another embodiment of this aspect of the invention, the method of blocking breast cancer intravasation, dissemination and metastasis comprises administering a composition of Formula I in combination with cisplatin.

In another embodiment of this aspect of the invention, the method of blocking breast cancer intravasation, dissemination and metastasis comprises administering a composition of Formula I in combination with carboplatin.

In another embodiment of this aspect of the invention, the method of blocking breast cancer intravasation, dissemination and metastasis comprises administering a composition of Formula I in combination with doxorubicin.

In another embodiment of this aspect of the invention, the method of blocking breast cancer intravasation, dissemination and metastasis comprises administering a composition of Formula I in combination with epirubicin.

In another embodiment of this aspect of the invention, the method of blocking breast cancer intravasation, dissemination and metastasis comprises administering a composition of Formula I in combination with tamoxifen.

In another embodiment of this aspect of the invention, the method of blocking breast cancer intravasation, dissemination and metastasis comprises administering a composition of Formula I in combination with fulvestrant.

In another embodiment of this aspect of the invention, the method of blocking breast cancer intravasation, dissemination and metastasis comprises administering a composition of Formula I in combination with anastrozole.

In another embodiment of this aspect of the invention, the method of blocking breast cancer intravasation, dissemination and metastasis comprises administering a composition of Formula I in combination with letrozole.

In another embodiment of this aspect of the invention, the method of blocking breast cancer intravasation, dissemination and metastasis comprises administering a composition of Formula I in combination with exemestane.

In another embodiment of this aspect of the invention, the method of blocking breast cancer intravasation, dissemination and metastasis comprises administering a composition of Formula I in combination with trastuzumab.

In another embodiment of this aspect of the invention, the method of blocking breast cancer intravasation, dissemination and metastasis comprises administering a composition of Formula I in combination with ado-trastuzumab emtansine.

In another embodiment of this aspect of the invention, the method of blocking breast cancer intravasation, dissemination and metastasis comprises the administration of a composition of Formula I in combination with pertuzumab.

In another embodiment of this aspect of the invention, the method of blocking breast cancer intravasation, dissemination and metastasis comprises administering a composition of Formula I in combination with lapatinib.

In another embodiment of this aspect of the invention, the method of blocking breast cancer intravasation, dissemination and metastasis comprises administering a composition of Formula I in combination with everolimus.

In another embodiment of this aspect of the invention, the method of blocking breast cancer intravasation, dissemination and metastasis comprises administering a composition of Formula I in combination with temsirolimus.

In another embodiment of this aspect of the invention, the method of blocking breast cancer intravasation, dissemination and metastasis comprises administering a composition of Formula I in combination with the CDK4/6 inhibitor LY2835219.

In another embodiment of this aspect of the invention, the method of blocking breast cancer intravasation, dissemination and metastasis comprises administering a composition of Formula I in combination with the CDK4/6 inhibitor LEE011.

In another embodiment of this aspect of the invention, the method of blocking breast cancer intravasation, dissemination and metastasis comprises administering a composition of Formula I in combination with the CDK4/6 inhibitor PD 0332991.

In another embodiment of this aspect of the invention, the method of blocking breast cancer intravasation, dissemination and metastasis comprises administering a composition of Formula I in combination with bevacizumab.

In another aspect of the invention, a method of blocking breast cancer intravasation, dissemination and metastasis comprises administration of a composition of Formula I at doses sufficient to block TIE2 kinase in the tumor microenvironment, wherein the dosing regimen of the composition of Formula I is administered as intermittent non-daily dosing. In some embodiments, the alternate daily dosing includes every third daily dosing, twice weekly dosing, or once weekly dosing.

In one embodiment of this aspect of the invention, a method of blocking breast cancer intravasation, dissemination and metastasis comprises the administration of a composition of Formula I at doses sufficient to block TIE2 kinase in the tumor microenvironment, with the dosing regimen of the composition of Formula I being administered twice weekly, once weekly, or alternate weekly.

In another embodiment of this aspect of the invention, a method of blocking breast cancer intravasation, dissemination and metastasis comprises the administration of a composition of Formula I at doses sufficient to block TIE2 kinase in the tumor microenvironment, with the dosing regimen of the composition of Formula I being administered twice weekly or once weekly.

In another embodiment of this aspect of the invention, a method of blocking breast cancer intravasation, dissemination and metastasis comprises the administration of a composition of Formula I at doses sufficient to block TIE2 kinase in the tumor microenvironment, with the dosing regimen of the composition of Formula I being administered twice weekly.

In another embodiment of this aspect of the invention, a method of blocking breast cancer intravasation, dissemination and metastasis comprises the administration of a composition of Formula I at doses sufficient to block TIE2 kinase in the tumor microenvironment administered in combination with one or more agents taken from an anti-tubulin agent, a DNA alkylating agent, a DNA synthesis-inhibiting agent, a DNA intercalating agent, an anti-estrogen agent, an anti-HER2 agent, a kinase inhibitor or an anti-angiogenic agent.

In another embodiment of this aspect of the invention, the method of blocking breast cancer intravasation, dissemination and metastasis comprises administering a composition of Formula I in combination with paclitaxel.

In another embodiment of this aspect of the invention, the method of blocking breast cancer intravasation, dissemination and metastasis comprises administering a composition of Formula I in combination with paclitaxel protein-bound particles for injectable suspension.

In another embodiment of this aspect of the invention, the method of blocking breast cancer intravasation, dissemination and metastasis comprises administering a composition of Formula I in combination with docetaxel.

In another embodiment of this aspect of the invention, the method of blocking breast cancer intravasation, dissemination and metastasis comprises the administration of a composition of Formula I in combination with eribulin.

In another embodiment of this aspect of the invention, the method of blocking breast cancer intravasation, dissemination and metastasis comprises the administration of a composition of Formula I in combination with ixabepilone.

In another embodiment of this aspect of the invention, the method of blocking breast cancer intravasation, dissemination and metastasis comprises the administration of a composition of Formula I in combination with vinorelbine.

In another embodiment of this aspect of the invention, the method of blocking breast cancer intravasation, dissemination and metastasis comprises the administration of a composition of Formula I in combination with capecitabine.

In another embodiment of this aspect of the invention, the method of blocking breast cancer intravasation, dissemination and metastasis comprises the administration of a composition of Formula I in combination with gemcitabine.

In another embodiment of this aspect of the invention, the method of blocking breast cancer intravasation, dissemination and metastasis comprises the administration of a composition of Formula I in combination with 5-fluorouracil.

In another embodiment of this aspect of the invention, the method of blocking breast cancer intravasation, dissemination and metastasis comprises the administration of a composition of Formula I in combination with methotrexate.

In another embodiment of this aspect of the invention, the method of blocking breast cancer intravasation, dissemination and metastasis comprises the administration of a composition of Formula I in combination with cyclophosphamide.

In another embodiment of this aspect of the invention, the method of blocking breast cancer intravasation, dissemination and metastasis comprises the administration of a composition of Formula I in combination with cisplatin.

In another embodiment of this aspect of the invention, the method of blocking breast cancer intravasation, dissemination and metastasis comprises the administration of a composition of Formula I in combination with carboplatin.

In another embodiment of this aspect of the invention, the method of blocking breast cancer intravasation, dissemination and metastasis comprises administering of a composition of Formula I in combination with doxorubicin.

In another embodiment of this aspect of the invention, the method of blocking breast cancer intravasation, dissemination and metastasis comprises administering of a composition of Formula I in combination with pegylated liposomal doxorubicin.

In another embodiment of this aspect of the invention, the method of blocking breast cancer intravasation, dissemination and metastasis comprises administering of a composition of Formula I in combination with epirubicin.

In yet another embodiment of this aspect of the invention, the method of blocking breast cancer intravasation, dissemination and metastasis comprises the administration of a composition of Formula I in combination with tamoxifen.

In another embodiment of this aspect of the invention, the method of blocking breast cancer intravasation, dissemination and metastasis comprises the administration of a composition of Formula I in combination with fulvestrant.

In another embodiment of this aspect of the invention, the method of blocking breast cancer intravasation, dissemination and metastasis comprises the administration of a composition of Formula I in combination with anastrozole.

In another embodiment of this aspect of the invention, the method of blocking breast cancer intravasation, dissemination and metastasis comprises the administration of a composition of Formula I in combination with letrozole.

In another embodiment of this aspect of the invention, the method of blocking breast cancer intravasation, dissemination and metastasis comprises the administration of a composition of Formula I in combination with exemestane.

In another embodiment of this aspect of the invention, the method of blocking breast cancer intravasation, dissemination and metastasis comprises the administration of a composition of Formula I in combination with trastuzumab.

In another embodiment of this aspect of the invention, the method of blocking breast cancer intravasation, dissemination and metastasis comprises the administration of a composition of Formula I in combination with ado-trastuzumab emtansine.

In another embodiment of this aspect of the invention, the method of blocking breast cancer intravasation, dissemination and metastasis comprises administering a composition of Formula I in combination with pertuzumab.

In another embodiment of this aspect of the invention, the method of blocking breast cancer intravasation, dissemination and metastasis comprises the administration of a composition of Formula I at doses sufficient to block TIE2 kinase in tumor microenvironment TIE2-expressing macrophages administered in combination with lapatinib.

In another embodiment of this aspect of the invention, the method of blocking breast cancer intravasation, dissemination and metastasis comprises the administration of a composition of Formula I at doses sufficient to block TIE2 kinase in tumor microenvironment TIE2-expressing macrophages administered in combination with everolimus.

In another embodiment of this aspect of the invention, the method of blocking breast cancer intravasation, dissemination and metastasis comprises the administration of a composition of Formula I at doses sufficient to block TIE2 kinase in tumor microenvironment TIE2-expressing macrophages administered in combination with temsirolimus.

In another embodiment of this aspect of the invention, the method of blocking breast cancer intravasation, dissemination and metastasis comprises the administration of a composition of Formula I at doses sufficient to block TIE2 kinase in tumor microenvironment TIE2-expressing macrophages administered in combination with the CDK4/6 inhibitor LY2835219.

In another embodiment of this aspect of the invention, the method of blocking breast cancer intravasation, dissemination and metastasis comprises the administration of a composition of Formula I at doses sufficient to block TIE2 kinase in tumor microenvironment TIE2-expressing macrophages administered in combination with the CDK4/6 inhibitor LEE011.

In another embodiment of this aspect of the invention, the method of blocking breast cancer intravasation, dissemination and metastasis comprises the administration of a composition of Formula I at doses sufficient to block TIE2 kinase in tumor microenvironment TIE2-expressing macrophages administered in combination with the CDK4/6 inhibitor PD 0332991.

In another embodiment of this aspect of the invention, the method of blocking breast cancer intravasation, dissemination and metastasis comprises the administration of a composition of Formula I in combination with bevacizumab.

Methods for Blocking Breast Cancer Immunotolerance:

Another aspect of the invention relates to a method of blocking breast cancer immunotolerance. The method comprises administering to a patient in need thereof an effective amount of a composition of Formula I. In one embodiment, the dosing regimen of the salt is sufficient to block TIE2 kinase in the tumor microenvironment that mediates immunotolerance.

In one embodiment of this aspect of the invention, the method of blocking breast cancer immunotolerance comprises administering to a patient in need thereof an effective amount of a composition of Formula I in a dosing regimen sufficient to block TIE2 kinase in the tumor microenvironment that mediates immunotolerance.

In one embodiment of this aspect of the invention, the method of blocking breast cancer immunotolerance comprises the administration of a composition of Formula I daily.

In another embodiment of this aspect of the invention, the composition of Formula I is administered in an intermittent non-daily manner. In some embodiments, the intermittent non-daily manner includes alternate daily dosing, every third daily dosing, twice weekly dosing, or once weekly dosing.

In another embodiment of this aspect of the invention, administration of the composition of Formula I is twice weekly, once weekly, or alternate weekly.

In another embodiment of this aspect of the invention, the composition of Formula I is administered twice weekly or once weekly.

In another embodiment of this aspect of the invention, the composition of Formula I is administered twice weekly.

In another embodiment of this aspect of the invention, the method of blocking breast cancer immunotolerance comprises administering to a patient in need thereof an effective amount of a composition of Formula I in a dosing regimen sufficient to block TIE2 kinase in the tumor microenvironment in combination with one or more agents taken from an anti-tubulin agent, a DNA alkylating agent, a DNA synthesis-inhibiting agent, a DNA intercalating agent, an anti-estrogen agent, an anti-HER2 agent, a kinase inhibitor, an anti-angiogenic agent, or an immunomodulating agent.

In another embodiment of this aspect of the invention, the method of blocking breast cancer immunotolerance comprises administering a composition of Formula I in combination with paclitaxel.

In another embodiment of this aspect of the invention, the method of blocking breast cancer immunotolerance comprises administering a composition of Formula I in combination with paclitaxel protein-bound particles for injectable suspension.

In another embodiment of this aspect of the invention, the method of blocking breast cancer immunotolerance comprises administering a composition of Formula I in combination with docetaxel.

In another embodiment of this aspect of the invention, the method of blocking breast cancer immunotolerance comprises the administration of a composition of Formula I in combination with eribulin.

In another embodiment of this aspect of the invention, the method of blocking breast cancer immunotolerance comprises the administration of a composition of Formula I in combination with ixabepilone.

In another embodiment of this aspect of the invention, the method of blocking breast cancer immunotolerance comprises the administration of a composition of Formula I in combination with vinorelbine.

In another embodiment of this aspect of the invention, the method of blocking breast cancer immunotolerance comprises the administration of a composition of Formula I in combination with capecitabine.

In another embodiment of this aspect of the invention, the method of blocking breast cancer immunotolerance comprises the administration of a composition of Formula I in combination with gemcitabine.

In another embodiment of this aspect of the invention, the method of blocking breast cancer immunotolerance comprises the administration of a composition of Formula I in combination with 5-fluorouracil.

In another embodiment of this aspect of the invention, the method of blocking breast cancer immunotolerance comprises the administration of a composition of Formula I in combination with 5-methotrexate.

In another embodiment of this aspect of the invention, the method of blocking breast cancer immunotolerance comprises the administration of a composition of Formula I in combination with cyclophosphamide.

In another embodiment of this aspect of the invention, the method of blocking breast cancer immunotolerance comprises the administration of a composition of Formula I in combination with cisplatin.

In another embodiment of this aspect of the invention, the method of blocking breast cancer immunotolerance comprises the administration of a composition of Formula I in combination with carboplatin.

In another embodiment of this aspect of the invention, the method of blocking breast cancer immunotolerance comprises administering of a composition of Formula I in combination with doxorubicin.

In another embodiment of this aspect of the invention, the method of blocking breast cancer immunotolerance comprises administering of a composition of Formula I in combination with pegylated liposomal doxorubicin.

In another embodiment of this aspect of the invention, the method of blocking breast cancer immunotolerance comprises administering of a composition of Formula I in combination with epirubicin.

In yet another embodiment of this aspect of the invention, the method of blocking breast cancer immunotolerance comprises the administration of a composition of Formula I in combination with tamoxifen.

In another embodiment of this aspect of the invention, the method of blocking breast cancer immunotolerance comprises the administration of a composition of Formula I in combination with fulvestrant.

In another embodiment of this aspect of the invention, the method of blocking breast cancer immunotolerance comprises the administration of a composition of Formula I in combination with anastrozole.

In another embodiment of this aspect of the invention, the method of blocking breast cancer immunotolerance comprises the administration of a composition of Formula I in combination with letrozole.

In another embodiment of this aspect of the invention, the method of blocking breast cancer immunotolerance comprises the administration of a composition of Formula I in combination with exemestane.

In another embodiment of this aspect of the invention, the method of blocking breast cancer immunotolerance comprises the administration of a composition of Formula I in combination with trastuzumab.

In another embodiment of this aspect of the invention, the method of blocking breast cancer immunotolerance comprises the administration of a composition of Formula I in combination with ado-trastuzumab emtansine.

In another embodiment of this aspect of the invention, the method of blocking breast cancer immunotolerance comprises administering a composition of Formula I in combination with pertuzumab.

In another embodiment of this aspect of the invention, the method of blocking breast cancer immunotolerance comprises the administration of a composition of Formula I at doses sufficient to block TIE2 kinase in tumor microenvironment TIE2-expressing macrophages administered in combination with lapatinib.

In another embodiment of this aspect of the invention, the method of blocking breast cancer immunotolerance comprises the administration of a composition of Formula I at doses sufficient to block TIE2 kinase in tumor microenvironment TIE2-expressing macrophages administered in combination with everolimus.

In another embodiment of this aspect of the invention, the method of blocking breast cancer immunotolerance comprises the administration of a composition of Formula I at doses sufficient to block TIE2 kinase in tumor microenvironment TIE2-expressing macrophages administered in combination with temsirolimus.

In another embodiment of this aspect of the invention, the method of blocking breast cancer immunotolerance comprises the administration of a composition of Formula I at doses sufficient to block TIE2 kinase in tumor microenvironment TIE2-expressing macrophages administered in combination with the CDK4/6 inhibitor LY2835219.

In another embodiment of this aspect of the invention, the method of blocking breast cancer immunotolerance comprises the administration of a composition of Formula I at doses sufficient to block TIE2 kinase in tumor microenvironment TIE2-expressing macrophages administered in combination with the CDK4/6 inhibitor LEE011.

In another embodiment of this aspect of the invention, the method of blocking breast cancer immunotolerance comprises the administration of a composition of Formula I at doses sufficient to block TIE2 kinase in tumor microenvironment TIE2-expressing macrophages administered in combination with the CDK4/6 inhibitor PD 0332991.

In another embodiment of this aspect of the invention, the method of blocking breast cancer immunotolerance comprises the administration of a composition of Formula I in combination with bevacizumab.

In another embodiment of this aspect of the invention, the method of blocking breast cancer immunotolerance comprises administering a composition of Formula I in combination with an anti-CTLA-4 agent.

In another embodiment of this aspect of the invention, the method of blocking breast cancer immunotolerance comprises administering a composition of Formula I in combination with ipilimumab.

In another embodiment of this aspect of the invention, the method of blocking breast cancer immunotolerance comprises administering a composition of Formula I in combination with an anti-PD-1 agent.

In another embodiment of this aspect of the invention, a method of blocking breast cancer immunotolerance comprises administering a composition of Formula I in combination with lambrolizumab.

In another embodiment of this aspect of the invention, the method of blocking breast cancer immunotolerance comprises administering a composition of Formula I in combination with an anti-PD L-1 agent.

In another embodiment of this aspect of the invention, the method of blocking breast cancer immunotolerance comprises administering a composition of Formula I in combination with MPDL3280A.

Methods for Blocking Breast Cancer Immunotolerance:

In another aspect of the invention, a method of blocking breast cancer immunotolerance comprises the administration of a composition of Formula I at doses sufficient to block TIE2 kinase in the tumor microenvironment, wherein the dosing regimen of the composition of Formula I is administered in an intermittent non-daily dosing manner, including alternate daily dosing, every third daily dosing, twice weekly dosing, or once weekly dosing.

In one embodiment of this aspect of the invention, a method of blocking breast cancer immunotolerance comprises the administration of a composition of Formula I at doses sufficient to block TIE2 kinase in the tumor microenvironment, wherein the composition of Formula I is administered twice weekly, once weekly, or alternate weekly.

In another embodiment of this aspect of the invention, a method of blocking breast cancer immunotolerance comprises the administration of a composition of Formula I at doses sufficient to block TIE2 kinase in the tumor microenvironment, wherein the composition of Formula I is administered twice weekly or once weekly.

In another embodiment of this aspect of the invention, a method of blocking breast cancer immunotolerance comprises the administration of a composition of Formula I at doses sufficient to block TIE2 kinase in the tumor microenvironment, wherein the composition of Formula I is administered twice weekly.

In another embodiment of this aspect of the invention, a method of blocking breast cancer immunotolerance comprises the administration of a composition of Formula I at doses sufficient to block TIE2 kinase in the tumor microenvironment administered in combination with one or more agents taken from an anti-tubulin agent, a DNA alkylating agent, a DNA synthesis-inhibiting agent, a DNA intercalating agent, an anti-estrogen agent, an anti-HER2 agent, a kinase inhibitor, an anti-angiogenic agent, or an immunomodulating agent.

In another embodiment of this aspect of the invention, the method of blocking breast cancer immunotolerance comprises administering a composition of Formula I in combination with paclitaxel.

In another embodiment of this aspect of the invention, the method of blocking breast cancer immunotolerance comprises administering a composition of Formula I in combination with paclitaxel protein-bound particles for injectable suspension.

In another embodiment of this aspect of the invention, the method of blocking breast cancer immunotolerance comprises administering a composition of Formula I in combination with docetaxel.

In another embodiment of this aspect of the invention, the method of blocking breast cancer immunotolerance comprises the administration of a composition of Formula I in combination with eribulin.

In another embodiment of this aspect of the invention, the method of blocking breast cancer immunotolerance comprises the administration of a composition of Formula I in combination with ixabepilone.

In another embodiment of this aspect of the invention, the method of blocking breast cancer immunotolerance comprises the administration of a composition of Formula I in combination with vinorelbine.

In another embodiment of this aspect of the invention, the method of blocking breast cancer immunotolerance comprises the administration of a composition of Formula I in combination with capecitabine.

In another embodiment of this aspect of the invention, the method of blocking breast cancer immunotolerance comprises the administration of a composition of Formula I in combination with gemcitabine.

In another embodiment of this aspect of the invention, the method of blocking breast cancer immunotolerance comprises the administration of a composition of Formula I in combination with 5-fluorouracil.

In another embodiment of this aspect of the invention, the method of blocking breast cancer immunotolerance comprises the administration of a composition of Formula I in combination with methotrexate.

In another embodiment of this aspect of the invention, the method of blocking breast cancer immunotolerance comprises the administration of a composition of Formula I in combination with cyclophosphamide.

In another embodiment of this aspect of the invention, the method of blocking breast cancer immunotolerance comprises the administration of a composition of Formula I in combination with cisplatin.

In another embodiment of this aspect of the invention, the method of blocking breast cancer immunotolerance comprises the administration of a composition of Formula I in combination with carboplatin.

In another embodiment of this aspect of the invention, the method of blocking breast cancer immunotolerance comprises administering of a composition of Formula I in combination with doxorubicin.

In another embodiment of this aspect of the invention, the method of blocking breast cancer immunotolerance comprises administering of a composition of Formula I in combination with pegylated liposomal doxorubicin.

In another embodiment of this aspect of the invention, the method of blocking breast cancer immunotolerance comprises administering of a composition of Formula I in combination with epirubicin.

In yet another embodiment of this aspect of the invention, the method of blocking breast cancer immunotolerance comprises the administration of a composition of Formula I in combination with tamoxifen.

In another embodiment of this aspect of the invention, the method of blocking breast cancer immunotolerance comprises the administration of a composition of Formula I in combination with fulvestrant.

In another embodiment of this aspect of the invention, the method of blocking breast cancer immunotolerance comprises the administration of a composition of Formula I in combination with anastrozole.

In another embodiment of this aspect of the invention, the method of blocking breast cancer immunotolerance comprises the administration of a composition of Formula I in combination with letrozole.

In another embodiment of this aspect of the invention, the method of blocking breast cancer immunotolerance comprises the administration of a composition of Formula I in combination with exemestane.

In another embodiment of this aspect of the invention, the method of blocking breast cancer immunotolerance comprises the administration of a composition of Formula I in combination with trastuzumab.

In another embodiment of this aspect of the invention, the method of blocking breast cancer immunotolerance comprises the administration of a a composition of Formula I in combination with ado-trastuzumab emtansine.

In another embodiment of this aspect of the invention, the method of blocking breast cancer immunotolerance comprises administering a composition of Formula I in combination with pertuzumab.

In another embodiment of this aspect of the invention, the method of blocking breast cancer immunotolerance comprises the administration of a composition of Formula I at doses sufficient to block TIE2 kinase in tumor microenvironment TIE2-expressing macrophages administered in combination with lapatinib.

In another embodiment of this aspect of the invention, the method of blocking breast cancer immunotolerance comprises the administration of a composition of Formula I at doses sufficient to block TIE2 kinase in tumor microenvironment TIE2-expressing macrophages administered in combination with everolimus.

In another embodiment of this aspect of the invention, the method of blocking breast cancer immunotolerance comprises the administration of a composition of Formula I at doses sufficient to block TIE2 kinase in tumor microenvironment TIE2-expressing macrophages administered in combination with temsirolimus.

In another embodiment of this aspect of the invention, the method of blocking breast cancer immunotolerance comprises the administration of a composition of Formula I at doses sufficient to block TIE2 kinase in tumor microenvironment TIE2-expressing macrophages administered in combination with the CDK4/6 inhibitor LY2835219.

In another embodiment of this aspect of the invention, the method of blocking breast cancer immunotolerance comprises the administration of a composition of Formula I at doses sufficient to block TIE2 kinase in tumor microenvironment TIE2-expressing macrophages administered in combination with the CDK4/6 inhibitor LEE011.

In another embodiment of this aspect of the invention, the method of blocking breast cancer immunotolerance comprises the administration of a composition of Formula I at doses sufficient to block TIE2 kinase in tumor microenvironment TIE2-expressing macrophages administered in combination with the CDK4/6 inhibitor PD 0332991.

In another embodiment of this aspect of the invention, the method of blocking breast cancer immunotolerance comprises the administration of a composition of Formula I in combination with bevacizumab.

In another embodiment of this aspect of the invention, the method of blocking breast cancer immunotolerance comprises administering a composition of Formula I in combination with an anti-CTLA-4 agent.

In another embodiment of this aspect of the invention, the method of blocking breast cancer immunotolerance comprises administering a composition of Formula I in combination with ipilimumab.

In another embodiment of this aspect of the invention, the method of blocking breast cancer immunotolerance comprises administering a composition of Formula I in combination with an anti-PD-1 agent.

In another embodiment of this aspect of the invention, a method of blocking breast cancer immunotolerance comprises administering a composition of Formula I in combination with lambrolizumab.

In another embodiment of this aspect of the invention, the method of blocking breast cancer immunotolerance comprises administering a composition of Formula I in combination with an anti-PD L-1 agent.

In another embodiment of this aspect of the invention, the method of blocking breast cancer immunotolerance comprises administering a composition of Formula I in combination with MPDL3280A.

Methods for Increasing Overall Survival in Breast Cancer Patients:

Another aspect of the invention relates to a method of increasing overall survival in breast cancer patients comprising administering to a patient in need thereof an effective amount of a composition of Formula I. In one embodiment, the dosing regimen is sufficient to block TIE2 kinase in the tumor microenvironment.

In another embodiment of this aspect of the invention, the method of increasing overall survival in breast cancer patients comprises a dosing regimen wherein the composition of Formula I administered daily.

In another embodiment of this aspect of the invention, the method of increasing overall survival in breast cancer patients comprises a composition of Formula I in a dosing regimen administered in an intermittent non-daily manner, including alternate daily dosing, every third daily dosing, twice weekly dosing, or once weekly dosing.

In another embodiment of this aspect of the invention, the method of increasing overall survival in breast cancer patients comprises a composition of Formula I in a dosing regimen administered twice weekly, once weekly, or alternate weekly.

In another embodiment of this aspect of the invention, the method of increasing overall survival in breast cancer patients, the dosing regimen of a composition of Formula I is administered twice weekly or once weekly.

In another embodiment of this aspect of the invention, the dosing regimen of a composition of Formula I is administered only twice weekly.

Another embodiment of this aspect of the invention relates to the method of increasing overall survival in breast cancer patients which comprises administering a composition of Formula I in a dosing regimen sufficient to block TIE2 kinase in the tumor microenvironment in combination with one or more agents taken from an anti-tubulin agent, a DNA alkylating agent, a DNA synthesis-inhibiting agent, a DNA intercalating agent, an anti-estrogen agent, an anti-HER2 agent, a kinase inhibitor, an anti-angiogenic agent, or an immunomodulating agent.

In another embodiment of this aspect of the invention, the method of increasing overall survival in breast cancer patients comprises administering a composition of Formula I in combination with paclitaxel.

In another embodiment of this aspect of the invention, the method of increasing overall survival in breast cancer patients comprises administering a composition of Formula I in combination with paclitaxel protein-bound particles for injectable suspension.

In another embodiment of this aspect of the invention, the method of increasing overall survival in breast cancer patients comprises administering a composition of Formula I in combination with docetaxel.

In another embodiment of this aspect of the invention, the method of increasing overall survival in breast cancer patients comprises the administration of a composition of Formula I in combination with eribulin.

In another embodiment of this aspect of the invention, the method of increasing overall survival in breast cancer patients comprises the administration of a composition of Formula I in combination with ixabepilone.

In another embodiment of this aspect of the invention, the method of increasing overall survival in breast cancer patients comprises the administration of a composition of Formula I in combination with vinorelbine.

In another embodiment of this aspect of the invention, the method of increasing overall survival in breast cancer patients comprises the administration of a composition of Formula I in combination with capecitabine.

In another embodiment of this aspect of the invention, the method of increasing overall survival in breast cancer patients comprises the administration of a composition of Formula I in combination with gemcitabine.

In another embodiment of this aspect of the invention, the method of increasing overall survival in breast cancer patients comprises the administration of a composition of Formula I in combination with 5-fluorouracil.

In another embodiment of this aspect of the invention, the method of increasing overall survival in breast cancer patients comprises the administration of a composition of Formula I in combination with methotrexate.

In another embodiment of this aspect of the invention, the method of increasing overall survival in breast cancer patients comprises the administration of a composition of Formula I in combination with cyclophosphamide.

In another embodiment of this aspect of the invention, the method of increasing overall survival in breast cancer patients comprises the administration of a composition of Formula I in combination with cisplatin.

In another embodiment of this aspect of the invention, the method of increasing overall survival in breast cancer patients comprises the administration of a composition of Formula I in combination with carboplatin.

In another embodiment of this aspect of the invention, the method of increasing overall survival in breast cancer patients comprises administering of a composition of Formula I in combination with doxorubicin.

In another embodiment of this aspect of the invention, the method of increasing overall survival in breast cancer patients comprises administering of a composition of Formula I in combination with pegylated liposomal doxorubicin.

In another embodiment of this aspect of the invention, the method of increasing overall survival in breast cancer patients comprises administering of a composition of Formula I in combination with epirubicin.

In yet another embodiment of this aspect of the invention, the method of increasing overall survival in breast cancer patients comprises the administration of a composition of Formula I in combination with tamoxifen.

In another embodiment of this aspect of the invention, the method of increasing overall survival in breast cancer patients comprises the administration of a composition of Formula I in combination with fulvestrant.

In another embodiment of this aspect of the invention, the method of increasing overall survival in breast cancer patients comprises the administration of a composition of Formula I in combination with anastrozole.

In another embodiment of this aspect of the invention, the method of increasing overall survival in breast cancer patients comprises the administration of a composition of Formula I in combination with letrozole.

In another embodiment of this aspect of the invention, the method of increasing overall survival in breast cancer patients comprises the administration of a composition of Formula I in combination with exemestane.

In another embodiment of this aspect of the invention, the method of increasing overall survival in breast cancer patients comprises the administration of a composition of Formula I in combination with trastuzumab.

In another embodiment of this aspect of the invention, the method of increasing overall survival in breast cancer patients comprises the administration of a composition of Formula I in combination with ado-trastuzumab emtansine.

In another embodiment of this aspect of the invention, the method of increasing overall survival in breast cancer patients comprises administering a composition of Formula I in combination with pertuzumab.

In another embodiment of this aspect of the invention, the method of increasing overall survival in breast cancer patients comprises the administration of a composition of Formula I at doses sufficient to block TIE2 kinase in tumor microenvironment TIE2-expressing macrophages administered in combination with lapatinib.

In another embodiment of this aspect of the invention, the method of increasing overall survival in breast cancer patients comprises the administration of a composition of Formula I at doses sufficient to block TIE2 kinase in tumor microenvironment TIE2-expressing macrophages administered in combination with everolimus.

In another embodiment of this aspect of the invention, the method of increasing overall survival in breast cancer patients comprises the administration of a composition of Formula I at doses sufficient to block TIE2 kinase in tumor microenvironment TIE2-expressing macrophages administered in combination with temsirolimus.

In another embodiment of this aspect of the invention, the method of increasing overall survival in breast cancer patients comprises the administration of a composition of Formula I at doses sufficient to block TIE2 kinase in tumor microenvironment TIE2-expressing macrophages administered in combination with the CDK4/6 inhibitor LY2835219.

In another embodiment of this aspect of the invention, the method of increasing overall survival in breast cancer patients comprises the administration of a composition of Formula I at doses sufficient to block TIE2 kinase in tumor microenvironment TIE2-expressing macrophages administered in combination with the CDK4/6 inhibitor LEE011.

In another embodiment of this aspect of the invention, the method of increasing overall survival in breast cancer patients comprises the administration of a composition of Formula I at doses sufficient to block TIE2 kinase in tumor microenvironment TIE2-expressing macrophages administered in combination with the CDK4/6 inhibitor PD 0332991.

In another embodiment of this aspect of the invention, the method of increasing overall survival in breast cancer patients comprises the administration of a composition of Formula I in combination with bevacizumab.

In another embodiment of this aspect of the invention, the method of increasing overall survival in breast cancer patients comprises administering a composition of Formula I in combination with an anti-CTLA-4 agent.

In another embodiment of this aspect of the invention, the method of increasing overall survival in breast cancer patients comprises administering a composition of Formula I in combination with ipilimumab.

In another embodiment of this aspect of the invention, the method of increasing overall survival in breast cancer patients comprises administering a composition of Formula I in combination with an anti-PD-1 agent.

In another embodiment of this aspect of the invention, the method of increasing overall survival in breast cancer patients comprises administering a composition of Formula I in combination with lambrolizumab.

In another embodiment of this aspect of the invention, the method of increasing overall survival in breast cancer patients comprises administering a composition of Formula I in combination with an anti-anti-PD L-1 agent.

In another embodiment of this aspect of the invention, the method of increasing overall survival in breast cancer patients comprises administering a composition of Formula I in combination with MPDL3280A.

Methods for Increasing Overall Survival in Breast Cancer Patients:

In another aspect of the invention, a method of increasing overall survival in breast cancer patients comprises the administration of a composition of Formula I at doses sufficient to block TIE2 kinase in the tumor microenvironment, wherein a dosing regimen of the composition of Formula I is intermittent non-daily dosing administration, including alternate daily dosing, every third daily dosing, twice weekly dosing, or once weekly dosing.

In one embodiment of this aspect of the invention, a method of increasing overall survival in breast cancer patients comprises the administration of a composition of Formula I at doses sufficient to block TIE2 kinase in the tumor microenvironment, wherein a dosing regimen of the composition of Formula I is twice weekly, once weekly, or alternate weekly, administration.

In another embodiment of this aspect of the invention, a method of increasing overall survival in breast cancer patients comprises the administration of a composition of Formula I at doses sufficient to block TIE2 kinase in the tumor microenvironment, wherein a dosing regimen of the composition of Formula I is twice weekly or once weekly administration.

In another embodiment of this aspect of the invention, a method of increasing overall survival in breast cancer patients comprises the administration of a composition of Formula I at doses sufficient to block TIE2 kinase in the tumor microenvironment, with a dosing regimen of the composition of Formula I is twice weekly administration.

In another embodiment of this aspect of the invention, a method of increasing overall survival in breast cancer patients comprises the administration of a composition of Formula I at doses sufficient to block TIE2 kinase in the tumor microenvironment administered in combination with one or more agents taken from an anti-tubulin agent, a DNA alkylating agent, a DNA synthesis-inhibiting agent, a DNA intercalating agent, an anti-estrogen agent, an anti-HER2 agent, a kinase inhibitor, an anti-angiogenic agent, or an immunomodulating agent.

In another embodiment of this aspect of the invention, the method of increasing overall survival in breast cancer patients administering a composition of Formula I in combination with paclitaxel.

In another embodiment of this aspect of the invention, the method of increasing overall survival in breast cancer patients comprises administering a composition of Formula I in combination with paclitaxel protein-bound particles for injectable suspension.

In another embodiment of this aspect of the invention, the method of increasing overall survival in breast cancer patients comprises administering a composition of Formula I in combination with docetaxel.

In another embodiment of this aspect of the invention, the method of increasing overall survival in breast cancer patients comprises the administration of a composition of Formula I in combination with eribulin.

In another embodiment of this aspect of the invention, the method of increasing overall survival in breast cancer patients comprises the administration of a composition of Formula I in combination with ixabepilone.

In another embodiment of this aspect of the invention, the method of increasing overall survival in breast cancer patients comprises the administration of a composition of Formula I in combination with vinorelbine.

In another embodiment of this aspect of the invention, the method of increasing overall survival in breast cancer patients comprises the administration of a composition of Formula I in combination with capecitabine.

In another embodiment of this aspect of the invention, the method of increasing overall survival in breast cancer patients comprises the administration of a composition of Formula I in combination with gemcitabine.

In another embodiment of this aspect of the invention, the method of increasing overall survival in breast cancer patients comprises the administration of a composition of Formula I in combination with 5-fluorouracil.

In another embodiment of this aspect of the invention, the method of increasing overall survival in breast cancer patients comprises the administration of a composition of Formula I in combination with methotrexate.

In another embodiment of this aspect of the invention, the method of increasing overall survival in breast cancer patients comprises the administration of a composition of Formula I in combination with cyclophosphamide.

In another embodiment of this aspect of the invention, the method of increasing overall survival in breast cancer patients comprises the administration of a composition of Formula I in combination with cisplatin.

In another embodiment of this aspect of the invention, the method of increasing overall survival in breast cancer patients comprises the administration of a composition of Formula I in combination with carboplatin.

In another embodiment of this aspect of the invention, the method of increasing overall survival in breast cancer patients comprises administering of a composition of Formula I in combination with doxorubicin.

In another embodiment of this aspect of the invention, the method of increasing overall survival in breast cancer patients comprises administering of a composition of Formula I in combination with pegylated liposomal doxorubicin.

In another embodiment of this aspect of the invention, the method of increasing overall survival in breast cancer patients comprises administering of a composition of Formula I in combination with epirubicin.

In yet another embodiment of this aspect of the invention, the method of increasing overall survival in breast cancer patients comprises the administration of a composition of Formula I in combination with tamoxifen.

In another embodiment of this aspect of the invention, the method of increasing overall survival in breast cancer patients comprises the administration of a composition of Formula I in combination with fulvestrant.

In another embodiment of this aspect of the invention, the method of increasing overall survival in breast cancer patients comprises the administration of a composition of Formula I in combination with anastrozole.

In another embodiment of this aspect of the invention, the method of increasing overall survival in breast cancer patients comprises the administration of a composition of Formula I in combination with letrozole.

In another embodiment of this aspect of the invention, the method of increasing overall survival in breast cancer patients comprises the administration of a composition of Formula I in combination with exemestane.

In another embodiment of this aspect of the invention, the method of increasing overall survival in breast cancer patients comprises the administration of a composition of Formula I in combination with trastuzumab.

In another embodiment of this aspect of the invention, the method of increasing overall survival in breast cancer patients comprises the administration of a composition of Formula I in combination with ado-trastuzumab emtansine.

In another embodiment of this aspect of the invention, the method of increasing overall survival in breast cancer patients comprises administering a composition of Formula I in combination with pertuzumab.

In another embodiment of this aspect of the invention, the method of increasing overall survival in breast cancer patients comprises the administration of a composition of Formula I at doses sufficient to block TIE2 kinase in tumor microenvironment TIE2-expressing macrophages administered in combination with lapatinib.

In another embodiment of this aspect of the invention, the method of increasing overall survival in breast cancer patients comprises the administration of a composition of Formula I at doses sufficient to block TIE2 kinase in tumor microenvironment TIE2-expressing macrophages administered in combination with everolimus.

In another embodiment of this aspect of the invention, the method of increasing overall survival in breast cancer patients comprises the administration of a composition of Formula I at doses sufficient to block TIE2 kinase in tumor microenvironment TIE2-expressing macrophages administered in combination with temsirolimus.

In another embodiment of this aspect of the invention, the method of increasing overall survival in breast cancer patients comprises the administration of a composition of Formula I at doses sufficient to block TIE2 kinase in tumor microenvironment TIE2-expressing macrophages administered in combination with the CDK4/6 inhibitor LY2835219.

In another embodiment of this aspect of the invention, the method of increasing overall survival in breast cancer patients comprises the administration of a composition of Formula I at doses sufficient to block TIE2 kinase in tumor microenvironment TIE2-expressing macrophages administered in combination with the CDK4/6 inhibitor LEE011.

In another embodiment of this aspect of the invention, the method of increasing overall survival in breast cancer patients comprises the administration of a composition of Formula I at doses sufficient to block TIE2 kinase in tumor microenvironment TIE2-expressing macrophages administered in combination with the CDK4/6 inhibitor PD 0332991.

In another embodiment of this aspect of the invention, the method of increasing overall survival in breast cancer patients comprises the administration of a composition of Formula I in combination with bevacizumab.

In another embodiment of this aspect of the invention, the method of increasing overall survival in breast cancer patients comprises administering a composition of Formula I in combination with an anti-CTLA-4 agent.

In another embodiment of this aspect of the invention, the method of increasing overall survival in breast cancer patients comprises administering a composition of Formula I in combination with ipilimumab.

In another embodiment of this aspect of the invention, the method of increasing overall survival in breast cancer patients comprises administering a composition of Formula I in combination with an anti-PD-1 agent.

In another embodiment of this aspect of the invention, the method of increasing overall survival in breast cancer patients comprises administering a composition of Formula I in combination with lambrolizumab.

In another embodiment of this aspect of the invention, the method of increasing overall survival in breast cancer patients comprises administering a composition of Formula I in combination with an anti-anti-PD L-1 agent.

In another embodiment of this aspect of the invention, the method of increasing overall survival in breast cancer patients comprises administering a composition of Formula I in combination with MPDL3280A.

Methods for Treating Breast Cancer Patients in a Neoadjuvant Setting Prior to Surgical Resection of Tumor:

Another aspect of the invention relates to a method of treating breast cancer patients in a neoadjuvant setting prior to surgical resection of tumor, comprising administering to a patient in need thereof and effective amount of a composition of Formula I, a dosing regimen of the composition of Formula I is sufficient to block TIE2 kinase in the tumor microenvironment.

In another embodiment of this aspect of the invention, the method of treating breast cancer patients in a neoadjuvant setting prior to surgical resection of tumor comprises administering to a patient in need thereof an effective amount of a composition of Formula I in a dosing regimen sufficient to block TIE2 kinase in the tumor microenvironment.

In another embodiment of this aspect of the invention, a method of treating breast cancer patients in a neoadjuvant setting prior to surgical resection comprises the administration of a composition of Formula I at doses sufficient to block TIE2 kinase in the tumor microenvironment, with a dosing regimen of the composition of Formula I being administered daily.

In another embodiment of this aspect of the invention, the method of treating breast cancer patients in a neoadjuvant setting prior to surgical resection comprises administering to a patient in need thereof an effective amount of a composition of Formula I in a dosing regimen sufficient to block TIE2 kinase in the tumor microenvironment, with a dosing regimen of the composition of Formula I administered in an intermittent non-daily manner, including alternate daily dosing, every third daily dosing, twice weekly dosing, or once weekly dosing.

In another embodiment of this aspect of the invention, the method of treating breast cancer patients in a neoadjuvant setting prior to surgical resection comprises administering to a patient in need thereof an effective amount of a composition of Formula I in a dosing regimen administered twice weekly, once weekly, or alternate weekly.

In another embodiment of this aspect of the invention, the method of treating breast cancer patients in a neoadjuvant setting prior to surgical resection comprises the administration of a composition of Formula I in a dosing regimen administered twice weekly or once weekly.

In another embodiment of this aspect of the invention, the dosing regimen of a composition of Formula I is administered twice weekly.

In another embodiment of this aspect of the invention, the method of treating breast cancer patients in a neoadjuvant setting prior to surgical resection comprises the administration of a composition of Formula I in dosing regimen sufficient to block TIE2 kinase in tumor microenvironment TIE2-expressing macrophages in combination with one or more agents taken from an anti-tubulin agent, a DNA alkylating agent, a DNA synthesis-inhibiting agent, a DNA intercalating agent, an anti-estrogen agent, an anti-HER2 agent, a kinase inhibitor, an anti-angiogenic agent, or an immunomodulating agent.

In another embodiment of this aspect of the invention, the method of treating breast cancer patients in a neoadjuvant setting prior to surgical resection of tumor comprises administering a composition of Formula I in combination with paclitaxel.

In another embodiment of this aspect of the invention, the method of treating breast cancer patients in a neoadjuvant setting prior to surgical resection of tumor comprises administering a composition of Formula I in combination with paclitaxel protein-bound particles for injectable suspension.

In another embodiment of this aspect of the invention, the method of treating breast cancer patients in a neoadjuvant setting prior to surgical resection of tumor comprises administering a composition of Formula I in combination with docetaxel.

In another embodiment of this aspect of the invention, the method of treating breast cancer patients in a neoadjuvant setting prior to surgical resection of tumor comprises the administration of a composition of Formula I in combination with eribulin.

In another embodiment of this aspect of the invention, the method of treating breast cancer patients in a neoadjuvant setting prior to surgical resection of tumor comprises the administration of a composition of Formula I in combination with ixabepilone.

In another embodiment of this aspect of the invention, the method of treating breast cancer patients in a neoadjuvant setting prior to surgical resection of tumor comprises the administration of a composition of Formula I in combination with vinorelbine.

In another embodiment of this aspect of the invention, the method of treating breast cancer patients in a neoadjuvant setting prior to surgical resection of tumor comprises the administration of a composition of Formula I in combination with capecitabine.

In another embodiment of this aspect of the invention, the method of treating breast cancer patients in a neoadjuvant setting prior to surgical resection of tumor comprises the administration of a composition of Formula I in combination with gemcitabine.

In another embodiment of this aspect of the invention, the method of treating breast cancer patients in a neoadjuvant setting prior to surgical resection of tumor comprises the administration of a composition of Formula I in combination with 5-fluorouracil.

In another embodiment of this aspect of the invention, the method of treating breast cancer patients in a neoadjuvant setting prior to surgical resection of tumor comprises the administration of a composition of Formula I in combination with methotrexate.

In another embodiment of this aspect of the invention, the method of treating breast cancer patients in a neoadjuvant setting prior to surgical resection of tumor comprises the administration of a composition of Formula I in combination with cyclophosphamide.

In another embodiment of this aspect of the invention, the method of treating breast cancer patients in a neoadjuvant setting prior to surgical resection of tumor comprises the administration of a composition of Formula I in combination with cisplatin.

In another embodiment of this aspect of the invention, the method of treating breast cancer patients in a neoadjuvant setting prior to surgical resection of tumor comprises the administration of a composition of Formula I in combination with carboplatin.

In another embodiment of this aspect of the invention, the method of treating breast cancer patients in a neoadjuvant setting prior to surgical resection of tumor comprises administering of a composition of Formula I in combination with doxorubicin.

In another embodiment of this aspect of the invention, the method of treating breast cancer patients in a neoadjuvant setting prior to surgical resection of tumor comprises administering of a composition of Formula I in combination with pegylated liposomal doxorubicin.

In another embodiment of this aspect of the invention, the method of treating breast cancer patients in a neoadjuvant setting prior to surgical resection of tumor comprises administering of a composition of Formula I in combination with epirubicin.

In yet another embodiment of this aspect of the invention, the method of treating breast cancer patients in a neoadjuvant setting prior to surgical resection of tumor comprises the administration of a composition of Formula I in combination with tamoxifen.

In another embodiment of this aspect of the invention, the method of treating breast cancer patients in a neoadjuvant setting prior to surgical resection of tumor comprises the administration of a composition of Formula I in combination with fulvestrant.

In another embodiment of this aspect of the invention, the method of treating breast cancer patients in a neoadjuvant setting prior to surgical resection of tumor comprises the administration of a composition of Formula I in combination with anastrozole.

In another embodiment of this aspect of the invention, the method of treating breast cancer patients in a neoadjuvant setting prior to surgical resection of tumor comprises the administration of a composition of Formula I in combination with letrozole.

In another embodiment of this aspect of the invention, the method of treating breast cancer patients in a neoadjuvant setting prior to surgical resection of tumor comprises the administration of a composition of Formula I in combination with exemestane.

In another embodiment of this aspect of the invention, the method of treating breast cancer patients in a neoadjuvant setting prior to surgical resection of tumor comprises the administration of a composition of Formula I in combination with trastuzumab.

In another embodiment of this aspect of the invention, the method of treating breast cancer patients in a neoadjuvant setting prior to surgical resection of tumor comprises the administration of a composition of Formula I in combination with ado-trastuzumab emtansine.

In another embodiment of this aspect of the invention, the method of treating breast cancer patients in a neoadjuvant setting prior to surgical resection of tumor comprises administering a composition of Formula I in combination with pertuzumab.

In another embodiment of this aspect of the invention, the method of treating breast cancer patients in a neoadjuvant setting prior to surgical resection of tumor comprises the administration of a composition of Formula I at doses sufficient to block TIE2 kinase in tumor microenvironment TIE2-expressing macrophages administered in combination with lapatinib.

In another embodiment of this aspect of the invention, the method of treating breast cancer patients in a neoadjuvant setting prior to surgical resection of tumor comprises the administration of a composition of Formula I at doses sufficient to block TIE2 kinase in tumor microenvironment TIE2-expressing macrophages administered in combination with everolimus.

In another embodiment of this aspect of the invention, the method of treating breast cancer patients in a neoadjuvant setting prior to surgical resection of tumor comprises the administration of a composition of Formula I at doses sufficient to block TIE2 kinase in tumor microenvironment TIE2-expressing macrophages administered in combination with temsirolimus.

In another embodiment of this aspect of the invention, the method of treating breast cancer patients in a neoadjuvant setting prior to surgical resection of tumor comprises the administration of a composition of Formula I at doses sufficient to block TIE2 kinase in tumor microenvironment TIE2-expressing macrophages administered in combination with the CDK4/6 inhibitor LY2835219.

In another embodiment of this aspect of the invention, the method of treating breast cancer patients in a neoadjuvant setting prior to surgical resection of tumor comprises the administration of a composition of Formula I at doses sufficient to block TIE2 kinase in tumor microenvironment TIE2-expressing macrophages administered in combination with the CDK4/6 inhibitor LEE011.

In another embodiment of this aspect of the invention, the method of treating breast cancer patients in a neoadjuvant setting prior to surgical resection of tumor comprises the administration of a composition of Formula I at doses sufficient to block TIE2 kinase in tumor microenvironment TIE2-expressing macrophages administered in combination with the CDK4/6 inhibitor PD 0332991.

In another embodiment of this aspect of the invention, the method of treating breast cancer patients in a neoadjuvant setting prior to surgical resection of tumor comprises the administration of a composition of Formula I in combination with bevacizumab.

In another embodiment of this aspect of the invention, the method of treating breast cancer patients in a neoadjuvant setting prior to surgical resection of tumor comprises administering a composition of Formula I in combination with an anti-CTLA-4 agent.

In another embodiment of this aspect of the invention, the method of treating breast cancer patients in a neoadjuvant setting prior to surgical resection of tumor comprises administering a composition of Formula I in combination with ipilimumab.

In another embodiment of this aspect of the invention, the method of treating breast cancer patients in a neoadjuvant setting prior to surgical resection of tumor comprises administering a composition of Formula I in combination with an anti-PD-1 agent.

In another embodiment of this aspect of the invention, the method of treating breast cancer patients in a neoadjuvant setting prior to surgical resection of tumor comprises administering a composition of Formula I in combination with lambrolizumab.

In another embodiment of this aspect of the invention, the method of treating breast cancer patients in a neoadjuvant setting prior to surgical resection of tumor comprises administering a composition of Formula I in combination with an anti-anti-PD L-1 agent.

In another embodiment of this aspect of the invention, the method of treating breast cancer patients in a neoadjuvant setting prior to surgical resection of tumor comprises administering a composition of Formula I in combination with MPDL3280A.

Methods for Treating Breast Cancer Patients in a Neoadjuvant Setting Prior to Surgical Resection:

In another aspect of the invention, a method of treating breast cancer patients in a neoadjuvant setting prior to surgical resection comprises the administration of a composition of Formula I at doses sufficient to block TIE2 kinase in the tumor microenvironment, with a dosing regimen of the composition of Formula I administered as intermittent non-daily dosing, including alternate daily dosing, every third daily dosing, twice weekly dosing, or once weekly dosing.

In one embodiment of this aspect of the invention, a method of treating breast cancer patients in a neoadjuvant setting prior to surgical resection comprises the administration of a composition of Formula I at doses sufficient to block TIE2 kinase in the tumor microenvironment, with a dosing regimen of the composition of Formula I administered twice weekly, once weekly, or alternate weekly.

In another embodiment of this aspect of the invention, a method of treating breast cancer patients in a neoadjuvant setting prior to surgical resection comprises the administration of a composition of Formula I at doses sufficient to block TIE2 kinase in the tumor microenvironment, with a dosing regimen of the composition of Formula I administered twice weekly or once weekly.

In another embodiment of this aspect of the invention, a method of treating breast cancer patients in a neoadjuvant setting prior to surgical resection comprises the administration of a composition of Formula I at doses sufficient to block TIE2 kinase in the tumor microenvironment, with a dosing regimen of the composition of Formula I administered twice weekly.

In another embodiment of this aspect of the invention, a method of treating breast cancer patients in a neoadjuvant setting prior to surgical resection comprises the administration of a composition of Formula I at doses sufficient to block TIE2 kinase in the tumor microenvironment administered in combination with one or more agents taken from an anti-tubulin agent, a DNA alkylating agent, a DNA synthesis-inhibiting agent, a DNA intercalating agent, an anti-estrogen agent, an anti-HER2 agent, a kinase inhibitor, an anti-angiogenic agent, or an immunomodulating agent.

In another embodiment of this aspect of the invention, the method of treating breast cancer patients in a neoadjuvant setting prior to surgical resection of tumor comprises administering a composition of Formula I in combination with paclitaxel.

In another embodiment of this aspect of the invention, the method of treating breast cancer patients in a neoadjuvant setting prior to surgical resection of tumor comprises administering a composition of Formula I in combination with paclitaxel protein-bound particles for injectable suspension.

In another embodiment of this aspect of the invention, the method of treating breast cancer patients in a neoadjuvant setting prior to surgical resection of tumor comprises administering a composition of Formula I in combination with docetaxel.

In another embodiment of this aspect of the invention, the method of treating breast cancer patients in a neoadjuvant setting prior to surgical resection of tumor comprises the administration of a composition of Formula I in combination with eribulin.

In another embodiment of this aspect of the invention, the method of treating breast cancer patients in a neoadjuvant setting prior to surgical resection of tumor comprises the administration of a composition of Formula I in combination with ixabepilone.

In another embodiment of this aspect of the invention, the method of treating breast cancer patients in a neoadjuvant setting prior to surgical resection of tumor comprises the administration of a composition of Formula I in combination with vinorelbine.

In another embodiment of this aspect of the invention, the method of treating breast cancer patients in a neoadjuvant setting prior to surgical resection of tumor comprises the administration of a composition of Formula I in combination with capecitabine.

In another embodiment of this aspect of the invention, the method of treating breast cancer patients in a neoadjuvant setting prior to surgical resection of tumor comprises the administration of a composition of Formula I in combination with gemcitabine.

In another embodiment of this aspect of the invention, the method of treating breast cancer patients in a neoadjuvant setting prior to surgical resection of tumor comprises the administration of a composition of Formula I in combination with 5-fluorouracil.

In another embodiment of this aspect of the invention, the method of treating breast cancer patients in a neoadjuvant setting prior to surgical resection of tumor comprises the administration of a composition of Formula I in combination with 5-methotrexate.

In another embodiment of this aspect of the invention, the method of treating breast cancer patients in a neoadjuvant setting prior to surgical resection of tumor comprises the administration of a composition of Formula I in combination with cyclophosphamide.

In another embodiment of this aspect of the invention, the method of treating breast cancer patients in a neoadjuvant setting prior to surgical resection of tumor comprises the administration of a composition of Formula I in combination with cisplatin.

In another embodiment of this aspect of the invention, the method of treating breast cancer patients in a neoadjuvant setting prior to surgical resection of tumor comprises the administration of a composition of Formula I in combination with carboplatin.

In another embodiment of this aspect of the invention, the method of treating breast cancer patients in a neoadjuvant setting prior to surgical resection of tumor comprises administering of a composition of Formula I in combination with doxorubicin.

In another embodiment of this aspect of the invention, the method of treating breast cancer patients in a neoadjuvant setting prior to surgical resection of tumor comprises administering of a composition of Formula I in combination with pegylated liposomal doxorubicin.

In another embodiment of this aspect of the invention, the method of treating breast cancer patients in a neoadjuvant setting prior to surgical resection of tumor comprises administering of a composition of Formula I in combination with epirubicin.

In yet another embodiment of this aspect of the invention, the method of treating breast cancer patients in a neoadjuvant setting prior to surgical resection of tumor comprises the administration of a composition of Formula I in combination with tamoxifen.

In another embodiment of this aspect of the invention, the method of treating breast cancer patients in a neoadjuvant setting prior to surgical resection of tumor comprises the administration of a composition of Formula I in combination with fulvestrant.

In another embodiment of this aspect of the invention, the method of treating breast cancer patients in a neoadjuvant setting prior to surgical resection of tumor comprises the administration of a composition of Formula I in combination with anastrozole.

In another embodiment of this aspect of the invention, the method of treating breast cancer patients in a neoadjuvant setting prior to surgical resection of tumor comprises the administration of a composition of Formula I in combination with letrozole.

In another embodiment of this aspect of the invention, the method of treating breast cancer patients in a neoadjuvant setting prior to surgical resection of tumor comprises the administration of a composition of Formula I in combination with exemestane.

In another embodiment of this aspect of the invention, the method of treating breast cancer patients in a neoadjuvant setting prior to surgical resection of tumor comprises the administration of a composition of Formula I in combination with trastuzumab.

In another embodiment of this aspect of the invention, the method of treating breast cancer patients in a neoadjuvant setting prior to surgical resection of tumor comprises the administration of a composition of Formula I in combination with ado-trastuzumab emtansine.

In another embodiment of this aspect of the invention, the method of treating breast cancer patients in a neoadjuvant setting prior to surgical resection of tumor comprises administering a composition of Formula I in combination with pertuzumab.

In another embodiment of this aspect of the invention, the method of treating breast cancer patients in a neoadjuvant setting prior to surgical resection of tumor comprises the administration of a composition of Formula I at doses sufficient to block TIE2 kinase in tumor microenvironment TIE2-expressing macrophages administered in combination with lapatinib.

In another embodiment of this aspect of the invention, the method of treating breast cancer patients in a neoadjuvant setting prior to surgical resection of tumor comprises the administration of a composition of Formula I at doses sufficient to block TIE2 kinase in tumor microenvironment TIE2-expressing macrophages administered in combination with everolimus.

In another embodiment of this aspect of the invention, the method of treating breast cancer patients in a neoadjuvant setting prior to surgical resection of tumor comprises the administration of a composition of Formula I at doses sufficient to block TIE2 kinase in tumor microenvironment TIE2-expressing macrophages administered in combination with temsirolimus.

In another embodiment of this aspect of the invention, the method of treating breast cancer patients in a neoadjuvant setting prior to surgical resection of tumor comprises the administration of a composition of Formula I at doses sufficient to block TIE2 kinase in tumor microenvironment TIE2-expressing macrophages administered in combination with the CDK4/6 inhibitor LY2835219.

In another embodiment of this aspect of the invention, the method of treating breast cancer patients in a neoadjuvant setting prior to surgical resection of tumor comprises the administration of a composition of Formula I at doses sufficient to block TIE2 kinase in tumor microenvironment TIE2-expressing macrophages administered in combination with the CDK4/6 inhibitor LEE011.

In another embodiment of this aspect of the invention, the method of treating breast cancer patients in a neoadjuvant setting prior to surgical resection of tumor comprises the administration of a composition of Formula I at doses sufficient to block TIE2 kinase in tumor microenvironment TIE2-expressing macrophages administered in combination with the CDK4/6 inhibitor PD 0332991.

In another embodiment of this aspect of the invention, the method of treating breast cancer patients in a neoadjuvant setting prior to surgical resection of tumor comprises the administration of a composition of Formula I in combination with bevacizumab.

In another embodiment of this aspect of the invention, the method of treating breast cancer patients in a neoadjuvant setting prior to surgical resection of tumor comprises administering a composition of Formula I in combination with an anti-CTLA-4 agent.

In another embodiment of this aspect of the invention, the method of treating breast cancer patients in a neoadjuvant setting prior to surgical resection of tumor comprises administering a composition of Formula I in combination with ipilimumab.

In another embodiment of this aspect of the invention, the method of treating breast cancer patients in a neoadjuvant setting prior to surgical resection of tumor comprises administering a composition of Formula I in combination with an anti-PD-1 agent.

In another embodiment of this aspect of the invention, the method of treating breast cancer patients in a neoadjuvant setting prior to surgical resection of tumor comprises administering a composition of Formula I in combination with lambrolizumab.

In another embodiment of this aspect of the invention, the method of treating breast cancer patients in a neoadjuvant setting prior to surgical resection of tumor comprises administering a composition of Formula I in combination with an anti-anti-PD L-1 agent.

In another embodiment of this aspect of the invention, the method of treating breast cancer patients in a neoadjuvant setting prior to surgical resection of tumor comprises administering a composition of Formula I in combination with MPDL3280A.

Another aspect of the invention relates to a method of treating ovarian cancer as TIE2 pathway signaling has been shown to contribute to ovarian cancer progression (Karlan et al, *J. Clinical Oncology* (2012) 30: 362-370). The method comprises administering to a patient in need thereof an effective amount of a composition of Formula I in a dosing regimen sufficient to block TIE2 kinase in the tumor microenvironment. In one embodiment of this aspect of the invention, a composition of Formula I is administered as a single agent.

In another embodiment of this aspect of the invention, a composition of Formula I is administered in combination with paclitaxel+carboplatin, doxetaxel+carboplatin, paclitaxel+cisplatin, or other taxane+platinum drug regimens.

Another aspect of the invention relates to a method of treating hepatocellular carcinoma as TIE2 pathway signaling has been shown to contribute to hepatocellular cancer progression and as a diagnostic marker (Matsubara et al, *Hepatology* (2013) 57: 1416-1425; Mitsuhashi et al, *Hepatology* (2003) 37: 1105-1113; Tanaka et al, *J. Clin Invest* (1999) 103: 341-345). The method comprises administering to a patient in need thereof an effective amount of a composition of Formula I in a dosing regimen sufficient to block TIE2 kinase in the tumor microenvironment.

In one embodiment of this aspect of the invention, a composition of Formula I is administered as a single agent.

In another embodiment of this aspect of the invention, a composition of Formula I is administered in combination with a kinase inhibitor including sorafenib, crizotinib, cabozantinib, sunitinib, pazopanib, sorafenib, regorafenib, or axitinib.

Another aspect of the invention relates to a method of treating glioma as TIE2 pathway signaling has been shown to contribute to glioma cancer progression (Liu et al, *Oncotarget* (2010) 1: 700-709; Brunckhorst et al, *Cancer Research* (2010) 70: 7283-7293). The method comprises administering to a patient in need thereof an effective amount of a composition of Formula I in a dosing regimen sufficient to block TIE2 kinase in the tumor microenvironment.

In one embodiment of this aspect of the invention, a composition of Formula I is administered as a single agent.

In another embodiment of this aspect of the invention, a composition of Formula I is administered in combination with radiotherapy.

In another embodiment of this aspect of the invention, a composition of Formula I is administered in combination with temozolomide therapy.

In another embodiment of this aspect of the invention, a composition of Formula I is administered in combination with radiotherapy and temozolomide therapy.

In another embodiment of this aspect of the invention, a composition of Formula I is administered in combination with bevacizumab therapy.

In another embodiment of this aspect of the invention, a composition of Formula I is administered in combination with radiotherapy and bevacizumab therapy.

In another embodiment of this aspect of the invention, a composition of Formula I is administered in combination with temozolomide therapy and bevacizumab therapy.

Another aspect of the invention relates to a method of treating melanoma as TIE2 pathway signaling has been shown to contribute to melanoma progression (Helfrich et al, *Clin Cancer Res* (2009) 15: 1384-1392; Peinado et al, *Nature Medicine* (2012) 18: 883-891). The method comprises administering to a patient in need thereof an effective amount of a composition of Formula I in a dosing regimen sufficient to block TIE2 kinase in the tumor microenvironment.

In one embodiment of this aspect of the invention, a composition of Formula I is administered as a single agent.

In another embodiment of this aspect of the invention, a composition of Formula I is administered in combination with vemurafenib.

In another embodiment of this aspect of the invention, a composition of Formula I is administered in combination with dabrafenib.

In another embodiment of this aspect of the invention, a composition of Formula I is administered in combination with dabrafenib and trametinib.

In another embodiment of this aspect of the invention, a composition of Formula I is administered in combination with temozolomide.

In another embodiment of this aspect of the invention, a composition of Formula I is administered in combination with dacarbazine.

In another embodiment of this aspect of the invention, a composition of Formula I is administered in combination with ipilimumab.

In another embodiment of this aspect of the invention, a composition of Formula I is administered in combination with labrolizumab or nivolumab.

In another embodiment of this aspect of the invention, a composition of Formula I is administered in combination with MPDL3280A.

In another embodiment of this aspect of the invention, a composition of Formula I is administered in combination with imatinib.

Another aspect of the invention relates to a method of treating colorectal cancer as TIE2 pathway signaling has been shown to contribute to colorectal cancer progression (Ahmad et al, *Cancer* (2001) 92: 1138-1143; Hashizume et al, *Cancer Research* (2010) 70: 2213-2223). The method comprises administering to a patient in need thereof an effective amount of a composition of Formula I in a dosing regimen sufficient to block TIE2 kinase in the tumor microenvironment.

In one embodiment of this aspect of the invention, a composition of Formula I is administered as a single agent.

In another embodiment of this aspect of the invention, a composition of Formula I is administered in combination with mFOLFOX6 therapy (oxaplatin+leucovorin+5-fluorouracil).

In another embodiment of this aspect of the invention, a composition of Formula I is administered in combination with mFOLFOX6 therapy and bevacizumab.

In another embodiment of this aspect of the invention, a composition of Formula I is administered in combination with mFOLFOX6 therapy and panitumumab.

In another embodiment of this aspect of the invention, a composition of Formula I is administered in combination with mFOLFOX6 therapy and cetuximab.

In another embodiment of this aspect of the invention, a composition of Formula I is administered in combination with capecitabine.

In another embodiment of this aspect of the invention, a composition of Formula I is administered in combination with capecitabine and bevacizumab.

In another embodiment of this aspect of the invention, a composition of Formula I is administered in combination with FOLFIRI therapy (irinotecan+leucovorin+5-fluorouracil).

In another embodiment of this aspect of the invention, a composition of Formula I is administered in combination with FOLFIRI therapy and bevacizumab.

In another embodiment of this aspect of the invention, a composition of Formula I is administered in combination with FOLFIRI therapy and aflibercept.

In another embodiment of this aspect of the invention, a composition of Formula I is administered in combination with FOLFIRI therapy and cetuximab.

In another embodiment of this aspect of the invention, a composition of Formula I is administered in combination with FOLFIRI therapy and panitumumab.

In another embodiment of this aspect of the invention, a composition of Formula I is administered in combination with panitumumab.

In another embodiment of this aspect of the invention, a composition of Formula I is administered in combination with panitumumab and irinotecan.

In another embodiment of this aspect of the invention, a composition of Formula I is administered in combination with cetuximab.

In another embodiment of this aspect of the invention, a composition of Formula I is administered in combination with cetuximab and irinotecan.

Another aspect of the invention relates to a method of treating acute myeloid leukemia as TIE2 pathway signaling has been shown to contribute to acute myeloid leukemia progression (Muller et al, *Leukemia Research* (2002) 26: 163-168; Hou et al, *Leukemia Research* (2008) 32: 904-912). The method comprises administering to a patient in need thereof an effective amount of a composition of Formula I in a dosing regimen sufficient to block TIE2 kinase in the tumor microenvironment.

In one embodiment of this aspect of the invention, a composition of Formula I is administered as a single agent.

In another embodiment of this aspect of the invention, a composition of Formula I is administered in combination with daunorubicin and cytarabine.

In another embodiment of this aspect of the invention, a composition of Formula I is administered in combination with idarubicin and cytarabine.

In another embodiment of this aspect of the invention, a composition of Formula I is administered in combination with mitoxantrone and cytarabine.

In another embodiment of this aspect of the invention, a composition of Formula I is administered in combination with cytarabine.

In another embodiment of this aspect of the invention, a composition of Formula I is administered in combination with 5-azacytabine.

In another embodiment of this aspect of the invention, a composition of Formula I is administered in combination with decitabine.

In another embodiment of this aspect of the invention, a composition of Formula I is administered in combination with quizartinib.

Another aspect of the invention relates to a method of treating cancer. The method comprises administering an effective amount of a composition of Formula I to a patient in need thereof. In one embodiment the patient overexpresses Tunica interna endothelial cell kinase 2 (TIE2) and the cancer is selected from breast cancer, colorectal cancer, hepatocellular carcinoma, head and neck cancer, bladder cancer, ovarian cancer, gliomas, angiosarcomas, melanomas, or acute myeloid leukemia.

In certain embodiments of the invention of the treatment regimen, the composition of Formula I is administered at a frequency of daily.

In other embodiments of the invention of the treatment regimen, the composition of Formula I is administered at a frequency of non-daily intermittent.

In other embodiments of the invention of the treatment regimen, the composition of Formula I is administered at a frequency of three times weekly.

In other embodiments of the invention of the treatment regimen, the composition of Formula I is administered at a frequency of two times weekly.

In other embodiments of the invention of the treatment regimen, the composition of Formula I is administered at a frequency of one time weekly.

In other embodiments of the invention of the treatment regimen, the composition of Formula I is administered at a frequency of one time every two weeks.

In other embodiments the cancer is metastatic, triple negative breast cancer (estrogen receptor negative, progesterone receptor negative, HER2 negative).

In other embodiments the cancer is estrogen positive ($ER^+$) and HER2 receptor kinase negative ($HER2^-$) breast cancer.

In other embodiments the cancer is inflammatory breast cancer.

In another embodiment, the method comprises the treatment of preventing or reducing one or more of primary tumor growth, tumor invasiveness, cancer intravasation, cancer dissemination, metastasis, and tumor immunotolerance. In certain embodiments the method increases patient survival rates.

Formulations, Administration, Dosing, and Treatment Regimens

The present invention includes the described salts of Formulae I and/or II (and/or additional agents) in various formulations. Any composition (and/or additional agents) described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the salts herein described can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

In one embodiment, the salts of Formulae I and/or II (and/or additional agents) described herein is formulated in accordance with routine procedures as a composition adapted for a mode of administration.

In certain embodiments, routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In some embodiments, the administering is effected orally or by parenteral injection. The mode of administration can be left to the discretion of the practitioner, and depend in-part upon the site of the medical condition. In most instances, administration results in the release of any agent described herein into the bloodstream.

In specific embodiments, it may be desirable to administer locally to the area in need of treatment or blocking.

In one embodiment, the salts (and/or additional agents) described herein is formulated in accordance with routine procedures as a composition adapted for oral administration to humans. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract, thereby providing a sustained action over an extended period of time. Selectively permeable membranes surrounding an osmotically active driving the salt of Formula I or II (and/or additional agents) described herein are also suitable for orally administered compositions. In these latter platforms, fluid from the environment surrounding the capsule is imbibed by the driving composition, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compositions, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

The dosage of the salt of Formulae I and/or II (and/or additional agents) described herein as well as the dosing schedule can depend on various parameters, including, but not limited to, the disease being treated, the subject's general health, and the administering physician's discretion. Any agent described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional therapeutic agent, to a subject in need thereof. In various embodiments any agent described herein is administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, or 11 hours to 12 hours apart.

The dosage of the salt of Formula I or II (and/or additional agents) described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

Generally, when orally administered to a mammal, the dosage of any composition of Formula I (and/or additional agents) described herein may be 0.001 mg/kg/day to 100 mg/kg/day, 0.01 mg/kg/day to 50 mg/kg/day, or 0.1 mg/kg/day to 10 mg/kg/day. When orally administered to a human, the dosage of any agent described herein is normally 0.001 mg to 1500 mg per day, 1 mg to 600 mg per day, or 5 mg to 30 mg per day. In some embodiments, the dosage of the salt (or agent) ranges from 57 mg to 1200 mg per day. In other embodiments, the dosage of the agents or salt ranges from 100 mg to 200 mg per day.

For administration of the salts of Formulae I or II (and/or additional agents) described herein by parenteral injection, the dosage is normally 0.1 mg to 250 mg per day, 1 mg to 20 mg per day, or 3 mg to 5 mg per day. Injections may be given up to four times daily. Generally, when orally or parenterally administered, the dosage of any agent described herein is normally 0.1 mg to 1500 mg per day, or 0.5 mg to 10 mg per day, or 0.5 mg to 5 mg per day. A dosage of up to 3000 mg per day can be administered.

Administration of the salts (and/or additional agents) described herein can, independently, be one to four times daily. Specifically, administration of the salt can be once a day at a dosing regimen of the salt is from about 50 mg to 1500 mg. Suitable daily dosage for the prophylactic effects sought is 57-1200 mg/day. If administered twice daily, a suitable dosage is 100 mg to 200 mg of the salt. Administration of the salt may also be intermittently non-daily. In particular, administration of the salt may be done one to four times per month or one to six times per year or once every two, three, four or five years. In certain embodiments administration of the salt is done weekly or bi-weekly. When administered weekly or bi-weekly, a suitable salt dosing regimen ranges from 50-200 mg/per administration. In certain weekly or bi-weekly administrations, dosage is 200-400 mg/per administration. Yet other mode of weekly or bi-weekly administration include 400-500 mg/per administration, 500-600 mg/per administration, 600-700 mg/per administration, 700-800 mg/per administration, 800-900 mg/per administration, 900-1000 mg/per administration, 1000-1100 mg/per administration, or 1100-1200 mg/per administration. Administration can be for the duration of one day or one month, two months, three months, six months, one year, two years, three years, and may even be for the life of the subject. Chronic, long-term administration will be indicated in many cases. The dosage may be administered as a single dose or divided into multiple doses. In general, the desired dosage should be administered at set intervals for a prolonged period, usually at least over several weeks or months, although longer periods of administration of several months or years or more may be needed.

EXAMPLES

Example 1

Biochemical inhibition of unphosphorylated TIE2 (uTIE2) by 1-(3-tert-butyl-1-(quinolin-6-yl)-1H-pyrazol-5-yl)-3-(2-fluoro-4-(2-(methylcarbamoyl)pyridin-4-yloxy)phenyl)urea Biochemical Assay for uTIE2 (Seq. ID No. 1)

Activity of uTIE2 kinase was determined by following the production of ADP from the kinase reaction through coupling with the pyruvate kinase/lactate dehydrogenase system (e.g., Schindler et al. *Science* (2000) 289: 1938-1942). In this assay, the oxidation of NADH (thus the decrease at $A_{340nm}$) was continuously monitored spectrophotometrically. The reaction mixture (100 µL) contained TIE2 (SignalChem) (5.6 nM), BSA (0.004% (w/v)), polyEY (1.5 mg/ml), $MgCl_2$ (15 mM), DTT (0.5 mM), pyruvate kinase (4 units), lactate dehydrogenase (7 units), phosphoenol pyruvate (1 mM), and NADH (0.28 mM) and ATP (1.5 mM) in 90 mM Tris buffer containing 0.2% octyl-glucoside and 1% DMSO, pH 7.5. The inhibition reaction was started by mixing serial diluted test composition with the above reaction mixture. The absorption at 340 nm was monitored continuously for 6 hours at 30° C. on a plate reader (BioTek). The reaction rate was calculated using the 5 to 6 h time frame. Percent inhibition was obtained by comparison of reaction rate with that of a control (i.e. with no test composition). $IC_{50}$ values were calculated from a series of percent inhibition values determined at a range of inhibitor concentrations using software routines as implemented in the GraphPad Prism software package. The composition 1-(3-tert-butyl-1-(quinolin-6-yl)-1H-pyrazol-5-yl)-3-(2-fluoro-4-(2-(methylcarbamoyl)pyridin-4-yloxy)phenyl)urea para-toluene sulfonic acid salt (compound 1 as described in figures) exhibited an $IC_{50}$ value of 3.5 nM.

uTIE2 Protein Sequence Used for Screening (Seq. ID No. 1)

QLKRANVQRRMAQAFQNVREEPAVQFNSGTLALNRKVKNNPDPTIYPVLD

WNDIKFQDVIGEGNFGQVLKARIKKDGLRMDAAIKRMKEYASKDDHRDFA

GELEVLCKLGHHPNIINLLGACEHRGYLYLAIEYAPHGNLLDFLRKSRVL

ETDPAFAIANSTASTLSSQQLLHFAADVARGMDYLSQKQFIHRDLAARNI

LVGENYVAKIADFGLSRGQEVYVKKTMGRLPVRWMAIESLNYSVYTTNSD

VWSYGVLLWEIVSLGGTPYCGMTCAELYEKLPQGYRLEKPLNCDDEVYDL

MRQCWREKPYERPSFAQILVSLNRMLEERKTYVNTTLYEKFTYAGIDCSA

EEAA

Example 2

Biochemical inhibition of phosphorylated TIE2 (pTIE2) by 1-(3-tert-butyl-1-(quinolin-6-yl)-1H-pyrazol-5-yl)-3-(2-fluoro-4-(2-(methylcarbamoyl)pyridin-4-yloxy)phenyl)urea Biochemical Assay for pTIE2 (Seq. ID No. 2)

Activity of pTIE2 kinase was determined by following the production of ADP from the kinase reaction through coupling with the pyruvate kinase/lactate dehydrogenase system (e.g., Schindler et al. Science (2000) 289: 1938-1942). In this assay, the oxidation of NADH (thus the decrease at $A_{340nm}$) was continuously monitored spectrophotometrically. The reaction mixture (100 µL) contained TIE2 (Life Technologies) (6 nM), BSA (0.004% (w/v)), polyEY (1.5 mg/ml), $MgCl_2$ (15 mM), DTT (0.5 mM), pyruvate kinase (4 units), lactate dehydrogenase (7 units), phosphoenol pyruvate (1 mM), and NADH (0.28 mM) and ATP (1.5 mM) in 90 mM Tris buffer containing 0.2% octyl-glucoside and 1% DMSO, pH 7.5. The inhibition reaction was started by mixing serial diluted test composition with the above reaction mixture. The absorption at 340 nm was monitored continuously for 6 hours at 30° C. on a plate reader (BioTek). The reaction rate was calculated using the 2 to 3 h time frame. Percent inhibition was obtained by comparison of reaction rate with that of a control (i.e. with no test composition). $IC_{50}$ values were calculated from a series of percent inhibition values determined at a range of inhibitor concentrations using software routines as implemented in the GraphPad Prism software package. When tested the compositions 1-(3-tert-butyl-1-(quinolin-6-yl)-1H-pyrazol-5-yl)-3-(2-fluoro-4-(2-(methylcarbamoyl)pyridin-4-yloxy)phenyl)urea para-toluene sulfonic acid salt and 1-(3-tert-butyl-1-(quinolin-6-yl)-1H-pyrazol-5-yl)-3-(2-fluoro-4-(2-(methylcarbamoyl)pyridin-4-yloxy)phenyl)urea bis-hydrochloric acid salt exhibited >50% inhibition of pTIE2 kinase at <0.1 µM concentration. 1-(3-tert-butyl-1-(quinolin-6-yl)-1H-pyrazol-5-yl)-3-(2-fluoro-4-(2-(methylcarbamoyl)pyridin-4-yloxy)phenyl)urea para-toluene sulfonic acid salt exhibited an $IC_{50}$ value of 4.2 nM. 1-(3-tert-butyl-1-(quinolin-6-yl)-1H-pyrazol-5-yl)-3-(2-fluoro-4-(2-(methylcarbamoyl)pyridin-4-yloxy)phenyl)urea bis-hydrochloric acid salt exhibited an $IC_{50}$ value of 2.2 nM.

pTIE2 Protein Sequence Used for Screening (Seq. ID No. 2)

PVLDWNDIKFQDVIGEGNFGQVLKARIKKDGLRMDAAIKRMKEYASKDDH

RDFAGELEVLCKLGHHPNIINLLGACEHRGYLYLAIEYAPHGNLLDFLRK

SRVLETDPAFAIANSTASTLSSQQLLHFAADVARGMDYLSQKQFIHRDLA

ARNILVGENYVAKIADFGLSRGQEVYVKKTMGRLPVRWMAIESLNYSVYT

TNSDVWSYGVLLWEIVSLGGTPYCGMTCAELYEKLPQGYRLEKPLNCDDE

VYDLMRQCWREKPYERPSFAQILVSLNRMLEERKT

Example 3

Cellular inhibition of TIE2 in CHO cells by 1-(3-tert-butyl-1-(quinolin-6-yl)-1H-pyrazol-5-yl)-3-(2-fluoro-4-(2-(methylcarbamoyl)pyridin-4-yloxy)phenyl)urea CHO-K1 Cell Culture CHO-K1 cells (catalog #CCL-61) were obtained from the American Type Culture Collection (ATCC, Manassas, Va.). Briefly, cells were grown in F12K medium supplemented with 10% characterized fetal bovine serum (Invitrogen, Carlsbad, Calif.), 100 units/mL penicillin G, 100 µg/ml streptomycin, and 0.29 mg/mL L-glutamine (Invitrogen, Carlsbad, Calif.) at 37 degrees Celsius, 5% $CO_2$, and 95% humidity. Cells were allowed to expand until reaching 70-95% confluence at which point they were subcultured or harvested for assay use.

TIE2-Transfected CHO K1 Phospho-TIE2 Western Blot Assay

CHO K1 cells ($1\times10^5$ cells/well) were added to a 24-well tissue-culture treated plate in 1 mL of RPMI1640 medium supplemented with 10% characterized fetal bovine serum and 1× non-essential amino acids (Invitrogen, Carlsbad, Calif.). Cells were then incubated overnight at 37 degrees Celsius, 5% $CO_2$, and 95% humidity. Medium was aspirated, and 0.5 mL of medium was added to each well. Transfection-grade plasmid DNA (TIE2 gene Gateway cloned into pcDNA3.2™/V5-DEST expression vector, Invitrogen, Carlsbad, Calif.) was diluted to 5 μg/mL in room temperature Opti-MEM® I Medium without serum (Invitrogen, Carlsbad, Calif.). Two μL of Lipofectamine LTX Reagent (Invitrogen, Carlsbad, Calif.) was added per 0.5 μg of plasmid DNA. The tube was mixed gently and incubated for 25 minutes at room temperature to allow for DNA-Lipofectamine LTX complex formation. 100 μL of the DNA-Lipofectamine LTX complex was added directly to each well containing cells and mixed gently. Twenty-four hours post-transfection, medium containing DNA-Lipofectamine complexes was aspirated, cells were washed with PBS, and RPMI1640 medium supplemented with 10% characterized fetal bovine serum (Invitrogen, Carlsbad, Calif.), and 1× non-essential amino acids (Invitrogen, Carlsbad, Calif.) was added. Test composition (1-(3-tert-butyl-1-(quinolin-6-yl)-1H-pyrazol-5-yl)-3-(2-fluoro-4-(2-(methylcarbamoyl)pyridin-4-yloxy)phenyl)urea para-toluene sulfonic acid salt) or DMSO was added to the wells (0.5% final DMSO concentration). The plates were then incubated for 4 hours at 37 degrees Celsius, 5% $CO_2$, and 95% humidity. Following the incubation, the media was aspirated and the cells were washed with PBS. The cells were lysed using MPER lysis buffer (Pierce, Rockford, Ill.) containing Halt Phosphatase and Protease Inhibitors (Pierce, Rockford, Ill.) and Phosphatase inhibitor cocktail 2 (Sigma, St. Louis, Mo.) at 4° C. for 10 minutes with shaking Cleared lysates were separated by SDS-PAGE on a 4-12% Novex NuPage Bis-Tris gel (Invitrogen, Carlsbad, Calif.) and then transferred to PVDF (Invitrogen, Carlsbad, Calif.). After transfer, the PVDF membrane was blocked with BSA (Santa Cruz Biotechnology, Santa Cruz, Calif.) and then probed with an antibody for phospho-TIE2 (Cell Signaling Technology, Beverly, Mass.). A secondary anti-rabbit antibody conjugated to horseradish peroxidase (Cell Signaling Technology, Beverly, Mass.) was used to detect phospho-TIE2. ECL Plus (GE Healthcare, Piscataway, N.J.), a substrate for horseradish peroxidase that generates a fluorescent product, was added. Fluorescence was detected using a Storm 840 phosphorimager (GE Healthcare, Piscataway, N.J.) in fluorescence mode. The 160 kDa phospho-TIE2 band was quantified using ImageQuant software (GE Healthcare, Piscataway, N.J.). Data was analyzed using Prism software (GraphPad Software, San Diego, Calif.) to calculate $IC_{50}$ values. The composition 1-(3-tert-butyl-1-(quinolin-6-yl)-1H-pyrazol-5-yl)-3-(2-fluoro-4-(2-(methylcarbamoyl)pyridin-4-yloxy)phenyl)urea para-toluene sulfonic acid salt exhibited an $IC_{50}$ value of 2.0 nM.

Example 4

Cellular inhibition of TIE2 in CHO cells after inhibitor wash-out by 1-(3-tert-butyl-1-(quinolin-6-yl)-1H-pyrazol-5-yl)-3-(2-fluoro-4-(2-(methylcarbamoyl)pyridin-4-yloxy)phenyl)urea CHO-K1 Cell Culture CHO-K1 cells (catalog #CCL-61) were obtained from the American Type Culture Collection (ATCC, Manassas, Va.). Briefly, cells were grown in F12K medium supplemented with 10% characterized fetal bovine serum (Invitrogen, Carlsbad, Calif.), 100 units/mL penicillin G, 100 μg/ml streptomycin, and 0.29 mg/mL L-glutamine (Invitrogen, Carlsbad, Calif.) at 37 degrees Celsius, 5% $CO_2$, and 95% humidity. Cells were allowed to expand until reaching 70-95% confluence at which point they were subcultured or harvested for assay use.

TIE2-Transfected CHO K1 Phospho-TIE2 Western Blot Composition Washout Assay

CHO K1 cells ($1\times10^5$ cells/well) were added to a 24-well tissue-culture treated plate in 1 mL of RPMI1640 medium supplemented with 10% characterized fetal bovine serum and 1× non-essential amino acids (Invitrogen, Carlsbad, Calif.). Cells were then incubated overnight at 37 degrees Celsius, 5% $CO_2$, and 95% humidity. Medium was aspirated, and 0.5 mL of medium was added to each well. Transfection-grade plasmid DNA (TIE2 gene Gateway cloned into pcDNA3.2™/V5-DEST expression vector, Invitrogen, Carlsbad, Calif.) was diluted to 5 μg/mL in room temperature Opti-MEM® I Medium without serum (Invitrogen, Carlsbad, Calif.). Two μL of Lipofectamine LTX Reagent (Invitrogen, Carlsbad, Calif.) was added per 0.5 μg of plasmid DNA. The tube was mixed gently and incubated for 25 minutes at room temperature to allow for DNA-Lipofectamine LTX complex formation. 100 μL of the DNA-Lipofectamine LTX complex was added directly to each well containing cells and mixed gently. Approximately 18-24 hours post-transfection, medium containing DNA-Lipofectamine complexes was aspirated, cells were washed with PBS, and RPMI1640 medium supplemented with 10% characterized fetal bovine serum (Invitrogen, Carlsbad, Calif.), and 1× non-essential amino acids (Invitrogen, Carlsbad, Calif.) was added. Test composition (1-(3-tert-butyl-1-(quinolin-6-yl)-1H-pyrazol-5-yl)-3-(2-fluoro-4-(2-(methylcarbamoyl)pyridin-4-yloxy)phenyl)urea para-toluene sulfonic acid salt) or DMSO was added to the wells (0.5% final DMSO concentration). The plates were then incubated for 2 hours at 37 degrees Celsius, 5% $CO_2$, and 95% humidity. Following the incubation, the media was aspirated and the cells were washed three times with 1 mL media to wash out free composition. Next, 1 mL fresh media was added and cells were incubated for specific times points prior to lysis (i.e., 0, 1, 2, 4, 6, and 24 hours). The cells were lysed using MPER lysis buffer (Pierce, Rockford, Ill.) containing Halt Phosphatase and Protease Inhibitors (Pierce, Rockford, Ill.) and Phosphatase inhibitor cocktail 2 (Sigma, St. Louis, Mo.) at 4° C. for 10 minutes with shaking Cleared lysates were separated by SDS-PAGE on a 4-12% Novex NuPage Bis-Tris gel (Invitrogen, Carlsbad, Calif.) and then transferred to PVDF (Invitrogen, Carlsbad, Calif.). After transfer, the PVDF membrane was blocked with BSA (Santa Cruz Biotechnology, Santa Cruz, Calif.) and then probed with an antibody for phospho-TIE2 (Cell Signaling Technology, Beverly, Mass.). A secondary anti-rabbit antibody conjugated to horseradish peroxidase (Cell Signaling Technology, Beverly, Mass.) was used to detect phospho-TIE2 ECL Plus (GE Healthcare, Piscataway, N.J.), a substrate for horseradish peroxidase that generates a fluorescent product, was added. Fluorescence was detected using a Storm 840 phosphorimager (GE Healthcare, Piscataway, N.J.) in fluorescence mode. PVDF membranes were stripped and then re-probed with total TIE2 antibody (Santa Cruz Biotechnology, Inc., Dallas, Tex.) as above. The 160 kDa phospho-TIE2 and total TIE2 bands were quantified using ImageQuant software (GE Healthcare, Piscataway, N.J.). Phospho-TIE2 levels were normalized to total TIE2 levels, and data was plotted using Prism software (GraphPad Software, San Diego, Calif.). When incubated with TIE2-transfected CHO K1 cells for 2 hours at 0.1 μM-1 μM prior to being washed out, Composition 1-(3-tert-butyl-1-(quinolin-6-yl)-1H-pyrazol-5-yl)-3-(2-fluoro-4-(2-(methylcarbamoyl)pyridin-4-yloxy)phenyl)urea para-toluene sulfonic acid salt disclosed herein exhibited >50% inhibition of phospho-TIE2 levels for >24 hours.

Example 5

Cellular inhibition of TIE2 in HUVEC cells by 1-(3-tert-butyl-1-(quinolin-6-yl)-1H-pyrazol-5-yl)-3-(2-fluoro-4-(2-(methylcarbamoyl)pyridin-4-yloxy)phenyl)urea HUVEC Cell Culture HUVEC (Human umbilical vein endothelial cells; Catalog #CRL-1730) cells were obtained from the American Type Culture Collection (ATCC, Manassas, Va.). Briefly, cells were grown in EGM-2 (Lonza, Walkersville, Md.) at 37 degrees Celsius, 5% $CO_2$, and 95% humidity. Cells were allowed to expand until reaching 90-95% saturation at which point they were subcultured or harvested for assay use.

HUVEC Phospho-TIE2 Western Blot Assay

HUVEC cells ($2.5 \times 10^5$ cells/well) were added to a 24-well tissue-culture treated plate in 1 mL of EGM-2 culture medium (Lonza, Walkersville, Md.). Cells were then incubated overnight at 37 degrees Celsius, 5% $CO_2$, and 95% humidity. Media was then aspirated and 1 mL EBM-2 basal medium (Lonza, Walkersville, Md.) supplemented with 2% FBS (Invitrogen, Carlsbad, Calif.) was added. Test composition or DMSO was added to the wells (0.5% final DMSO concentration). The plates were then incubated for 4 hours at 37 degrees Celsius, 5% $CO_2$, and 95% humidity. During the incubation, histidine-tagged angiopoietin 1 (ANG1) growth factor (R&D Systems, Minneapolis, Minn.) was added to a anti-polyhistidine antibody (R&D Systems, Minneapolis, Minn.) for 30 minutes at room temperature to generate multimers of ANG1. Following the four hour incubation of composition, cells were stimulated with 800 ng/mL of the ANG1/anti-polyhistidine antibody complex mixture for 15 minutes. The media was aspirated and the cells were washed with PBS. The cells were lysed using MPER lysis buffer (Pierce, Rockford, Ill.) containing Halt Phosphatase and Protease Inhibitors (Pierce, Rockford, Ill.) and Phosphatase inhibitor cocktail 2 (Sigma, St. Louis, Mo.) at 4° C. for 10 minutes with shaking Cleared lysates were separated by SDS-PAGE on a 4-12% Novex NuPage Bis-Tris gel (Invitrogen, Carlsbad, Calif.) and then transferred to PVDF (Invitrogen, Carlsbad, Calif.). After transfer, the PVDF membrane was blocked with BSA (Santa Cruz Biotechnology, Santa Cruz, Calif.) and then probed with an antibody for phospho-TIE2 (Cell Signaling Technology, Beverly, Mass.). A secondary anti-rabbit antibody conjugated to horseradish peroxidase (Cell Signaling Technology, Beverly, Mass.) was used to detect phospho-TIE2. ECL Plus (GE Healthcare, Piscataway, N.J.), a substrate for horseradish peroxidase that generates a fluorescent product, was added. Fluorescence was detected using a Storm 840 phosphorimager (GE Healthcare, Piscataway, N.J.) in fluorescence mode. The 160 kDa phospho-TIE2 band was quantified using ImageQuant software (GE Healthcare, Piscataway, N.J.). Data was analyzed using Prism software (GraphPad Software, San Diego, Calif.) to calculate $IC_{50}$ values. The composition 1-(3-tert-butyl-1-(quinolin-6-yl)-1H-pyrazol-5-yl)-3-(2-fluoro-4-(2-(methylcarbamoyl)pyridin-4-yloxy)phenyl)urea para-toluene sulfonic acid salt disclosed herein exhibited an $IC_{50}$ value of 0.018 nM.

Example 6

Inhibition of angiopoietin 1 (ANG1) or angiopoietin 2 (ANG2) stimulated capillary tube formation by 1-(3-tert-butyl-1-(quinolin-6-yl)-1H-pyrazol-5-yl)-3-(2-fluoro-4-(2-(methylcarbamoyl)pyridin-4-yloxy)phenyl)urea HMVEC Cell Culture HMVEC (Human microvascular endothelial cells; Catalog #PCS-110-010) cells were obtained from the American Type Culture Collection (ATCC, Manassas, Va.). Briefly, cells were grown in EGM-2 MV (Lonza, Walkersville, Md.) at 37 degrees Celsius, 5% $CO_2$, and 95% humidity. Cells were allowed to expand until reaching 90-95% saturation at which point they were subcultured or harvested for assay use.

HMVEC Capillary Tube Formation Assay

HMVEC cells ($1.5 \times 10^4$ cells/well) mixed with test composition or DMSO control and the appropriate growth factor (ANG1 or ANG2) or control were added to a 96-well tissue-culture treated plate coated with growth-factor reduced Matrigel in 0.1 mL of EBM-2 basal medium (Lonza, Walkersville, Md.). Cells were then incubated for 18 hours at 37 degrees Celsius, 5% $CO_2$, and 95% humidity. Media was then gently aspirated and wells were gently washed with 0.1 mL EBM-2 basal medium. Media was again aspirated and 1 μM Calcein AM solution (Invitrogen, Carlsbad, Calif.) in basal medium was added to each well to fluorescently label live cells. Cells were then incubated for 30 minutes at 37 degrees Celsius, 5% $CO_2$, and 95% humidity. Media was aspirated and wells were gently washed with phosphate-buffered saline twice. Images of each well were acquired with a fluorescent microscope and processed using ImagePro Analyzer (Media Cybernetics, Inc., Rockville, Md.) using an automated macro that measures total capillary tube length. Data was analyzed using Prism software (GraphPad Software, San Diego, Calif.) to calculate $IC_{50}$ values. The composition 1-(3-tert-butyl-1-(quinolin-6-yl)-1H-pyrazol-5-yl)-3-(2-fluoro-4-(2-(methylcarbamoyl)pyridin-4-yloxy)phenyl)urea para-toluene sulfonic acid salt disclosed herein exhibited an $IC_{50}$ value of 6.9 nM for inhibition of ANG1-stimulated HMVEC capillary tube formation. The composition of Formula I disclosed herein exhibited an $IC_{50}$ value of 34 nM for inhibition of ANG2-stimulated HMVEC capillary tube formation.

Example 7

Inhibition of in vivo primary tumor growth and invasiveness in the murine PyMT breast cancer model by 1-(3-tert-butyl-1-(quinolin-6-yl)-1H-pyrazol-5-yl)-3-(2-fluoro-4-(2-(methylcarbamoyl)pyridin-4-yloxy)phenyl)urea as a single agent and in combination with paclitaxel PyMT Syngeneic Breast Cancer Model Primary Tumor Growth The PyMT syngeneic breast cancer implant mouse model was used to evaluate in vivo activity of compound 1. Briefly, $1 \times 10^6$ cells (dissociated from PyMT tumor fragments) in 0.1 mL total volume were implanted into the fourth mammary fat pad on the left side of female mice (FVB/NJ, JAXWEST: RB05 mice from Jackson Labs). A total of 10 mice were implanted in each group. Molecular Imaging, Inc.'s Animal Care and Use Committee approved all the experimental protocols and conducted experiments in compliance with all the laws, regulations and guidelines of the National Institutes of Health (NIH). Treatment was initiated by oral administration (gavage) of Compound 1 twice daily or vehicle (0.4% hydroxypropylmethylcellulose in water) and/or intravenous administration (IV) of paclitaxel every five days or vehicle (10% ethanol, 10% Cremophor EL and 80% saline) according to individual body weight on the day of treatment at 0.2 mL per 20 g when tumor size reached approximately 850 mg. Animals were dosed for 21 days. Body weights and tumor measurements were recorded three times weekly. Tumor burden (mg) was estimated from caliper measurements by the formula for the volume of a prolate ellipsoid assuming unit density as: Tumor burden $(mg)=(L \times W^2)/2$, where L and W are the respective orthogonal tumor length and width measurements (mm). In the PyMT model, both Compound 1 and paclitaxel groups evidenced tumor growth inhibition. Compound 1 in combination with paclitaxel demonstrated additive activity (FIG. 1). These data evidence in vivo activity by Compound 1 and show correlation to enzymatic and cell data.

Example 8

Inhibition of in vivo primary tumor macrophage accumulation in the murine PyMT breast cancer model by 1-(3-tert-butyl-1-(quinolin-6-yl)-1H-pyrazol-5-yl)-3-(2-fluoro-4-(2-(methylcarbamoyl)pyridin-4-yloxy)phenyl)urea as a single agent and in combination with paclitaxel PyMT Syngeneic Breast Cancer Model Primary Tumor Macrophage Accumulation The PyMT syngeneic breast cancer implant mouse model was used to evaluate in vivo activity of compound 1. Briefly, $1 \times 10^6$ cells (dissociated from PyMT tumor fragments) in 0.1 mL total volume were implanted into the fourth mammary fat pad on the left side of female mice (FVB/NJ, JAXWEST: RB05 mice from Jackson Labs). A total of 10 mice were implanted in each group. Molecular Imaging, Inc.'s Animal Care and Use Committee approved all the experimental protocols and conducted experiments in compliance with all the laws, regulations and guidelines of the National Institutes of Health (NIH). Treatment was initiated by oral administration (gavage) of Compound 1 twice daily or vehicle (0.4% hydroxypropylmethylcellulose in water) and/or intravenous administration (IV) of paclitaxel every five days or vehicle (10% ethanol, 10% Cremophor EL and 80% saline) according to individual body weight on the day of treatment at 0.2 mL per 20 g when tumor size reached approximately 850 mg. Animals were dosed for 21 days. Body weights and tumor measurements were recorded three times weekly.

Figure 2:
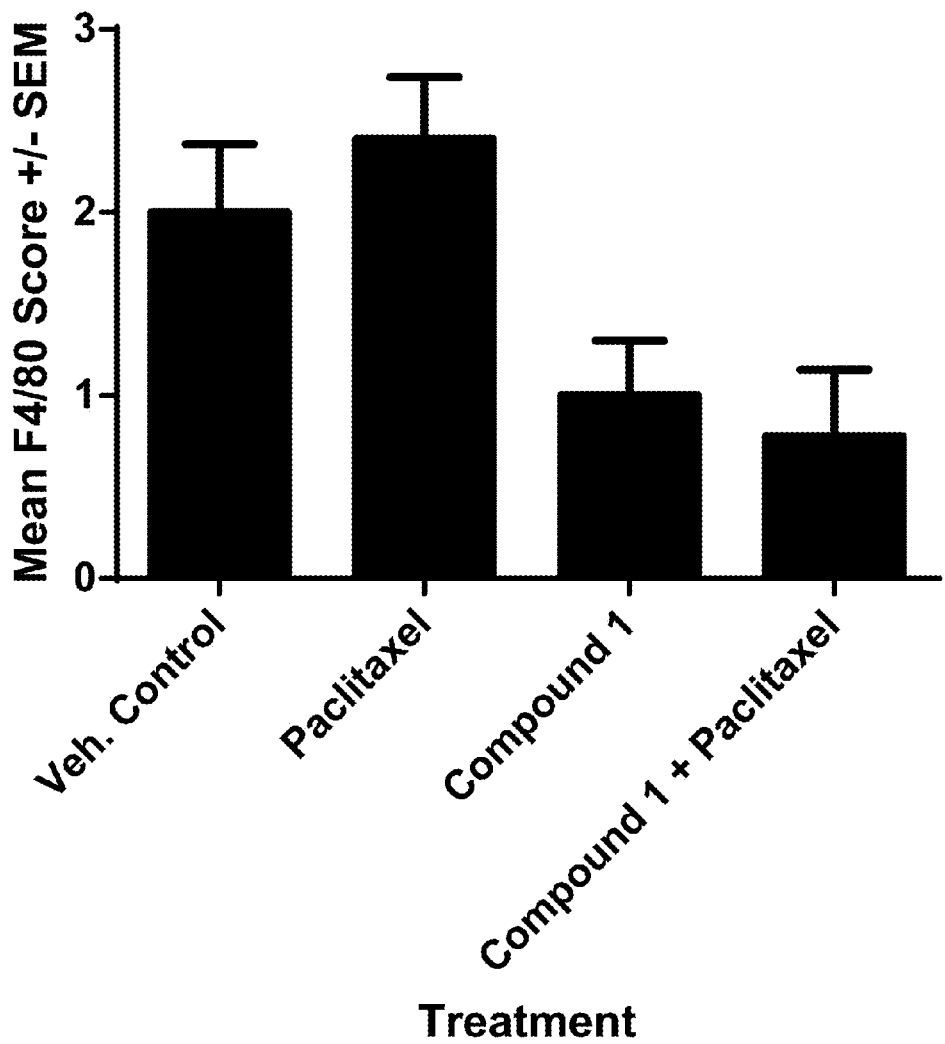
FIG. 2 shows the inhibition of PyMT tumor macrophage accumulation using the composition of Formula II, paclitaxel, or a combination thereof.

At the end of study, tumors were excised and placed in formalin. Formalin-fixed tumor samples were then placed in paraffin blocks. Formalin fixed-paraffin embedded tissue slides were deparaffinized with xylene and hydrated to distilled water through a graduated series of alcohol rinses. Antigenic retrieval was performed using Dako's PT Link Module with a Tris/EDTA buffer target retrieval solution at 95° C. for 20 minutes. Once the slides cooled down, they were loaded onto a Dako AutostainerPlusLink for immunohistochemical staining at room temperature with F4/80 and CD31 antibodies, to stain for macrophages and endothelial cells, respectively. Endogenous peroxidase and alkaline phosphatase activity in the tissues was quenched with a Dual Endogenous Enzyme Block solution (Dako, S2003) for 5 minutes. Non-specific protein binding was blocked with serum free Protein Block (Dako, X0909) for 5 minutes. The rat anti mouse CD31 primary antibody was then incubated on the experimental tissue sections for 30 minutes at an immunogenic concentration of 1:100. The primary antibody was then conjugated with a rabbit anti rat immunoglobulin secondary antibody (Dako, E0468). The secondary antibody was then amplified with a goat anti rabbit peroxidase labeled polymer (Dako, K4003) for 30 minutes. Enzymatic staining was developed with substrate-chromogen DAB+ (Dako, K3468) for 5 minutes. Excess rat IgG components were further blocked with Rodent Block Rat (Biocare Medical, RBR962H) for 5 minutes. The rat anti mouse F4/80 primary antibody was incubated on the experimental tissue sections for 30 minutes. The F4/80 was then conjugated with a rabbit anti rat immunoglobulin secondary antibody (Dako, E0468). The secondary antibody was then amplified with a goat anti rabbit alkaline phosphatase labeled polymer, (Biocare RALP525) for 30 minutes. Enzymatic staining was developed with substrate chromogen WARP Red (Biocare WR806). The counter staining was performed with automation hematoxylin for 10 minutes. The tissue slides were then air dried and cleared to xylene for glass cover slipping. Slides were scored for F4/80 staining using a scale of 0, no visible staining; 1, weak staining; 2, moderate staining; 3 strong staining. In the PyMT model, Compound 1 evidenced a decrease in macrophage accumulation at the primary tumor, whereas paclitaxel did not decrease macrophage accumulation. Compound 1 in combination with paclitaxel demonstrated similar activity to Compound 1 single-agent treatment (FIG. 2). These data evidence in vivo activity by Compound 1 and show correlation to enzymatic and cell data.

Example 9

Inhibition of in vivo primary tumor TIE2 cell accumulation in the murine PyMT breast cancer model by 1-(3-tert-butyl-1-(quinolin-6-yl)-1H-pyrazol-5-yl)-3-(2-fluoro-4-(2-(methylcarbamoyl)pyridin-4-yloxy)phenyl)urea as a single agent and in combination with paclitaxel PyMT Syngeneic Breast Cancer Model Primary Tumor Macrophage Accumulation The PyMT syngeneic breast cancer implant mouse model was used to evaluate in vivo activity of compound 1. Briefly, $1 \times 10^6$ cells (dissociated from PyMT tumor fragments) in 0.1 mL total volume were implanted into the fourth mammary fat pad on the left side of female mice (FVB/NJ, JAXWEST: RB05 mice from Jackson Labs). A total of 10 mice were implanted in each group. Molecular Imaging, Inc.'s Animal Care and Use Committee approved all the experimental protocols and conducted experiments in compliance with all the laws, regulations and guidelines of the National Institutes of Health (NIH). Treatment was initiated by oral administration (gavage) of Compound 1 twice daily or vehicle (0.4% hydroxypropylmethylcellulose in water) and/or intravenous administration (IV) of paclitaxel every five days or vehicle (10% ethanol, 10% Cremophor EL and 80% saline) according to individual body weight on the day of treatment at 0.2 mL per 20 g when tumor size reached approximately 850 mg. Animals were dosed for 21 days. Body weights and tumor measurements were recorded three times weekly.

Figure 3:
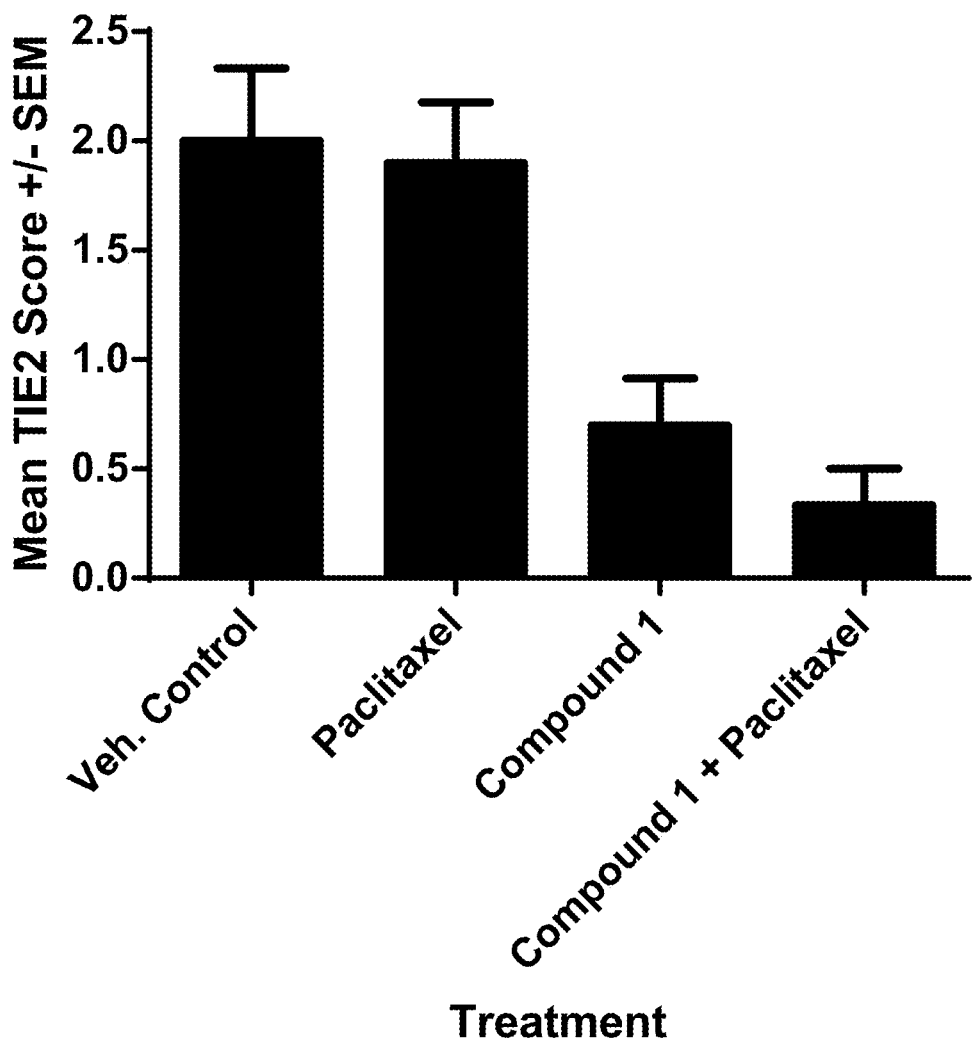
FIG. 3 shows the inhibition of PyMT tumor TIE2-expressing cell accumulation using the composition of Formula II, paclitaxel, or a combination thereof.

At the end of study, tumors were excised and placed in formalin. Formalin-fixed tumor samples were then placed in paraffin blocks. The experimental formalin fixed-paraffin embedded tissue slides were deparaffinized with xylene and hydrated to distilled water through a graduated series of alcohol rinses. Antigenic retrieval was performed using Dako's PT Link Module with a Citrate pH 6 buffer target retrieval solution at 95° C. for 20 minutes. Once the slides cooled down, they were loaded onto a Dako AutostainerPlusLink for immunohistochemical staining at room temperature with both TIE2 and CD31 antibodies. Endogenous peroxidase and alkaline phosphatase activity in the tissues was quenched with a Dual Endogenous Enzyme Block solution (Dako, S2003) for 5 minutes. Non-specific protein binding was blocked with serum free Protein Block (Dako, X0909) for 5 minutes. The rat anti mouse CD31 primary antibody was then incubated on the experimental tissue sections for 30 minutes at an immunogenic concentration of 1:100. The primary antibody was then conjugated with a rabbit anti rat immunoglobulin secondary antibody (Dako, E0468). The secondary antibody was then amplified with a goat anti rabbit peroxidase labeled polymer (Dako, K4003) for 30 minutes. Enzymatic staining was developed with substrate-chromogen DAB+(Dako, K3468) for 5 minutes. Excess protein components were further blocked with Protein Block (Dako, X0909) for 5 minutes. The rabbit anti TIE2 primary antibody was incubated on the experimental tissue sections for 30 minutes. The TIE2 antibody was then conjugated with an alkaline phosphatase labeled goat anti rabbit polymer for 30 minutes. Enzymatic staining was developed with substrate chromogen WARP Red (Biocare WR806). The counter staining was performed with automation hematoxylin for 10 minutes. The tissue slides were then air dried and cleared to xylene for glass cover slipping. Slides were scored for TIE2 staining using a scale of 0, no visible staining; 1, weak staining; 2, moderate staining; 3 strong staining. In the PyMT model, Compound 1 evidenced a decrease in TIE2-expressing cell accumulation at the primary tumor, whereas paclitaxel did not decrease TIE2-expressing cell accumulation. Compound 1 in combination with paclitaxel demonstrated enhanced activity compared to Compound 1 single-agent treatment (FIG. 3). These data evidence in vivo activity by Compound 1 and show correlation to enzymatic and cell data.

Example 10

Inhibition of in vivo lung metastases in the murine PyMT breast cancer model by 1-(3-tert-butyl-1-(quinolin-6-yl)-1H-pyrazol-5-yl)-3-(2-fluoro-4-(2-(methylcarbamoyl)pyridin-4-yloxy)phenyl)urea as a single agent and in combination with paclitaxel PyMT Syngeneic Breast Cancer Model Lung Metastasis Evaluation The PyMT syngeneic breast cancer implant mouse model was used to evaluate in vivo activity of compound 1. Briefly, $1\times10^6$ cells (dissociated from PyMT tumor fragments) in 0.1 mL total volume were implanted into the fourth mammary fat pad on the left side of female mice (FVB/NJ, JAXWEST: RB05 mice from Jackson Labs). A total of 10 mice were implanted in each group. Molecular Imaging, Inc.'s Animal Care and Use Committee approved all the experimental protocols and conducted experiments in compliance with all the laws, regulations and guidelines of the National Institutes of Health (NIH). Treatment was initiated by oral administration (gavage) of Compound 1 twice daily or vehicle (0.4% hydroxypropylmethylcellulose in water) and/ or intravenous administration (IV) of paclitaxel every five days or vehicle (10% ethanol, 10% Cremophor EL and 80% saline) according to individual body weight on the day of treatment at 0.2 mL per 20 g when tumor size reached approximately 850 mg. Animals were dosed for 21 days. Body weights and tumor measurements were recorded three times weekly.

Figure 4:
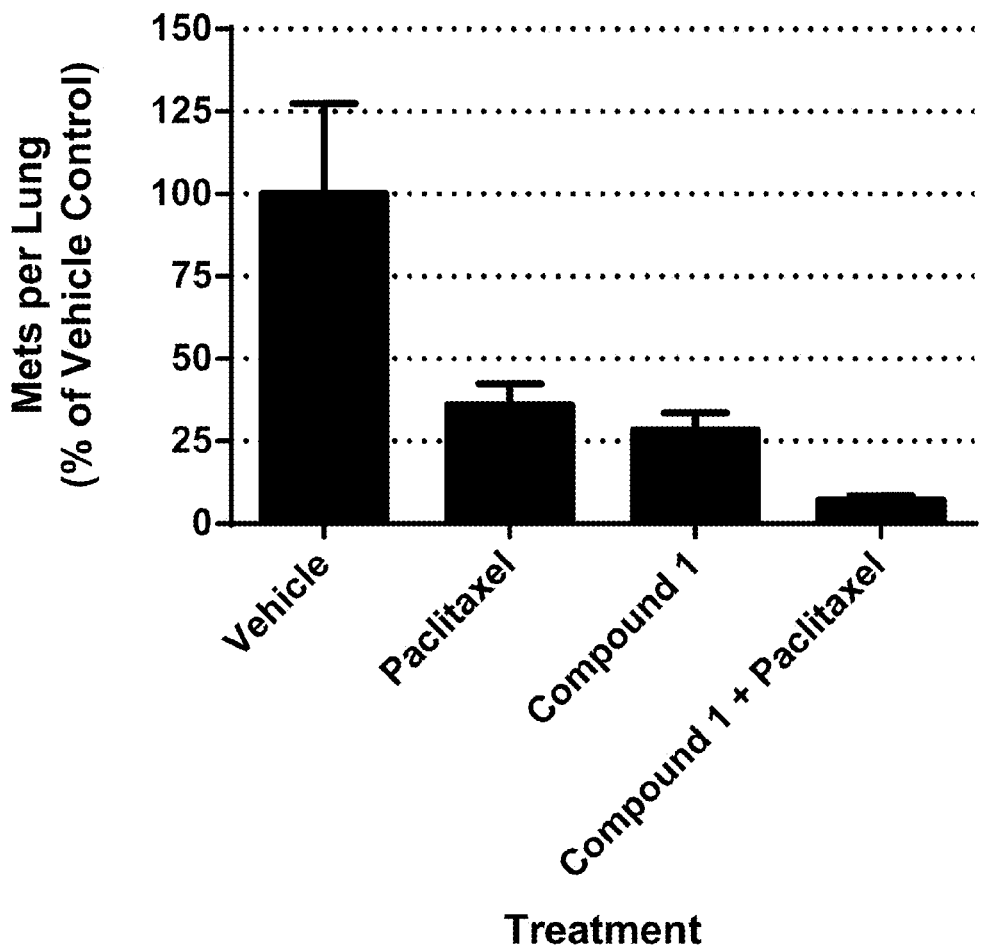
FIG. 4 shows the inhibition of lung metastases in the PyMT breast cancer model using the composition of Formula II, paclitaxel, or a combination thereof.

At the end of study, lung tissues were excised and placed in formalin. Formalin-fixed lung samples were then placed in paraffin blocks. Each lung block had three slides with two levels per slide cut and stained with Hematoxylin and Eosin. Metastatic lung nodules were counted via microscopy. In the PyMT model, both Compound 1 and paclitaxel evidenced a similar decrease in lung metastasis. Compound 1 in combination with paclitaxel demonstrated additive activity compared to single-agent treatments (FIG. 4). These data evidence in vivo activity by Compound 1 and show correlation to enzymatic and cell data.

Example 11

Inhibition of in vivo lung metastases in the murine PyMT breast cancer model by 1-(3-tert-butyl-1-(quinolin-6-yl)-1H-pyrazol-5-yl)-3-(2-fluoro-4-(2-(methylcarbamoyl)pyridin-4-yloxy)phenyl)urea dosed intermittently (non-daily) in combination with paclitaxel PyMT Syngeneic Breast Cancer Model Lung Metastasis Evaluation The PyMT syngeneic breast cancer implant mouse model was used to evaluate in vivo activity of compound 1. Briefly, $1\times10^6$ cells (dissociated from PyMT tumor fragments and stored frozen in cell-freezing medium) in 0.1 mL total volume were implanted into the fourth mammary fat pad on the left side of female mice (FVB/NJ, JAXWEST:RB05 mice from Jackson Labs). A total of three mice were implanted in each group. Molecular Imaging, Inc.'s Animal Care and Use Committee approved all the experimental protocols and conducted experiments in compliance with all the laws, regulations and guidelines of the National Institutes of Health (NIH). Treatment was initiated by oral administration (gavage) of Compound 1 twice weekly or vehicle (0.4% hydroxypropylmethylcellulose in water) and/ or intravenous administration (IV) of paclitaxel every five days or vehicle (10% ethanol, 10% Cremophor EL and 80% saline) according to individual body weight on the day of treatment at 0.2 mL per 20 g when tumor size reached approximately 600 mg. Animals were dosed for 12 days. Body weights and tumor measurements were recorded three times weekly.

Figure 5:
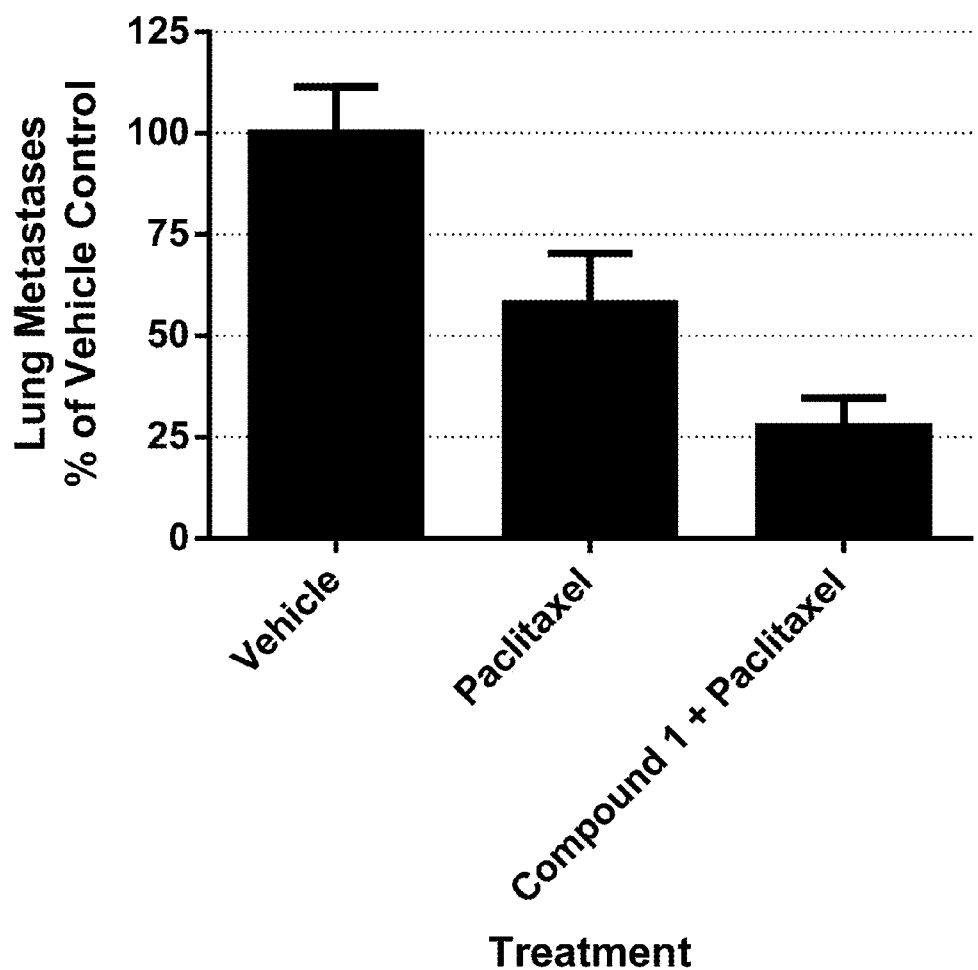
FIG. 5 shows the inhibition of lung metastases in the PyMT breast cancer model comparing the activities of paclitaxel and the combination of paclitaxel and the composition of Formula II.

At the end of study, lung tissues were excised and placed in formalin. Formalin-fixed lung samples were then placed in paraffin blocks. Each lung block had three slides with two levels per slide cut and stained with Hematoxylin and Eosin. Metastatic lung nodules were counted via microscopy. In the PyMT model, paclitaxel evidenced a decrease in lung metastasis. Compound 1 in combination with paclitaxel demonstrated additive activity compared to single-agent treatment (FIG. 5). These data evidence in vivo activity by Compound 1 and show correlation to enzymatic and cell data.

Example 12

Inhibition of in vivo lung metastases in the murine PyMT breast cancer model by 1-(3-tert-butyl-1-(quinolin-6-yl)-1H-pyrazol-5-yl)-3-(2-fluoro-4-(2-(methylcarbamoyl)pyridin-4-yloxy)phenyl)urea dosed intermittently (non-daily) in combination with eribulin PyMT Syngeneic Breast Cancer Model Lung Metastasis Evaluation The PyMT syngeneic breast cancer implant mouse model was used to evaluate in vivo activity of compound 1. Briefly, $1 \times 10^6$ cells (dissociated from PyMT tumor fragments and stored frozen in cell-freezing medium) in 0.1 mL total volume were implanted into the fourth mammary fat pad on the left side of female mice (FVB/NJ, JAXWEST:RB05 mice from Jackson Labs). A total of three mice were implanted in each group. Molecular Imaging, Inc.'s Animal Care and Use Committee approved all the experimental protocols and conducted experiments in compliance with all the laws, regulations and guidelines of the National Institutes of Health (NIH). Treatment was initiated by oral administration (gavage) of Compound 1 twice weekly or vehicle (0.4% hydroxypropylmethylcellulose in water) and/or intravenous administration (IV) of eribulin three times weekly or vehicle (80% saline) according to individual body weight on the day of treatment at 0.2 mL per 20 g when tumor size reached approximately 600 mg. Animals were dosed for 12 days. Body weights and tumor measurements were recorded three times weekly.

Figure 6:
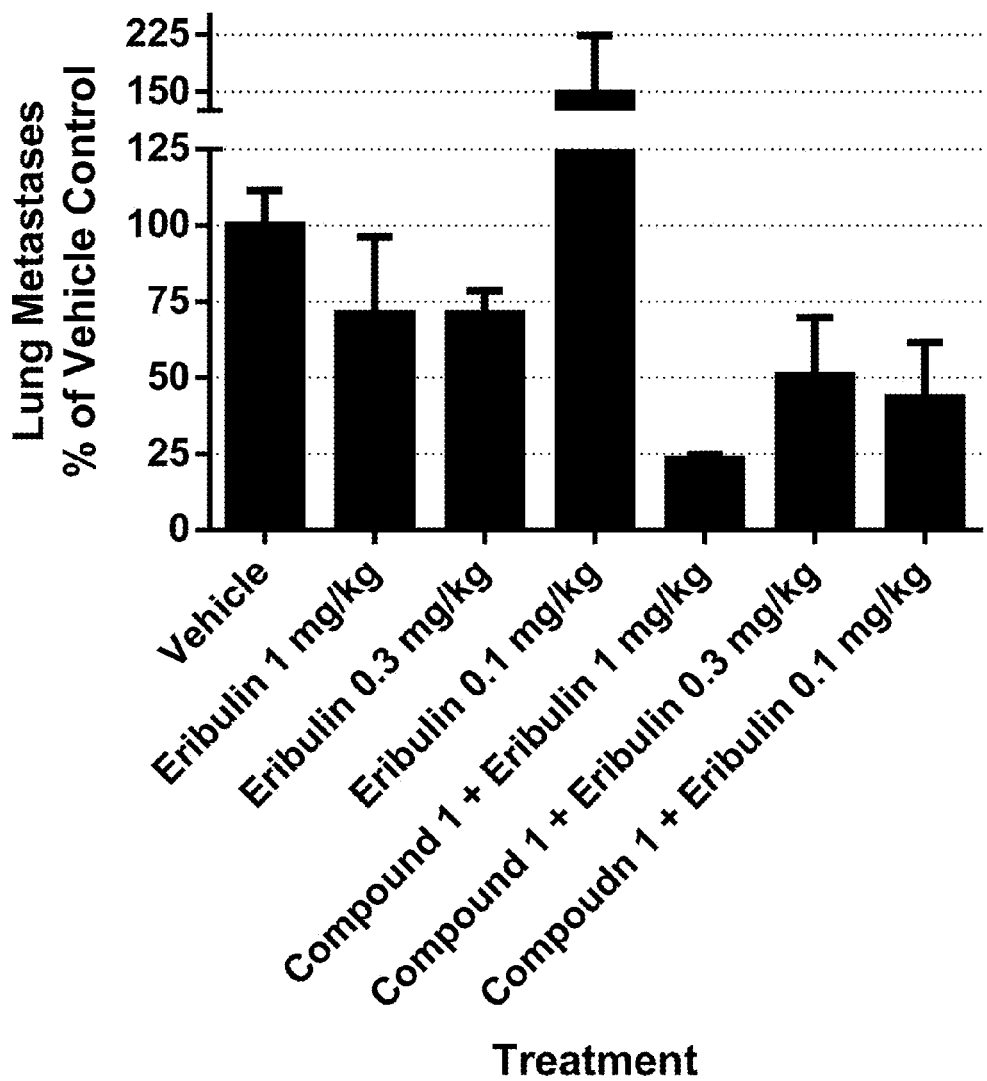
FIG. 6 shows the inhibition of lung metastases in the PyMT breast cancer model using eribulin as a single agent or in combination with the composition of Formula II.

At the end of study, lung tissues were excised and placed in formalin. Formalin-fixed lung samples were then placed in paraffin blocks. Each lung block had three slides with two levels per slide cut and stained with Hematoxylin and Eosin. Metastatic lung nodules were counted via microscopy. In the PyMT model, eribulin evidenced a decrease (or increase at low dose) in lung metastasis. Compound 1 in combination with eribulin demonstrated additive activity compared to single-agent treatment (FIG. 6). These data evidence in vivo activity by Compound 1 and show correlation to enzymatic and cell data.

Example 13

Figure 7:
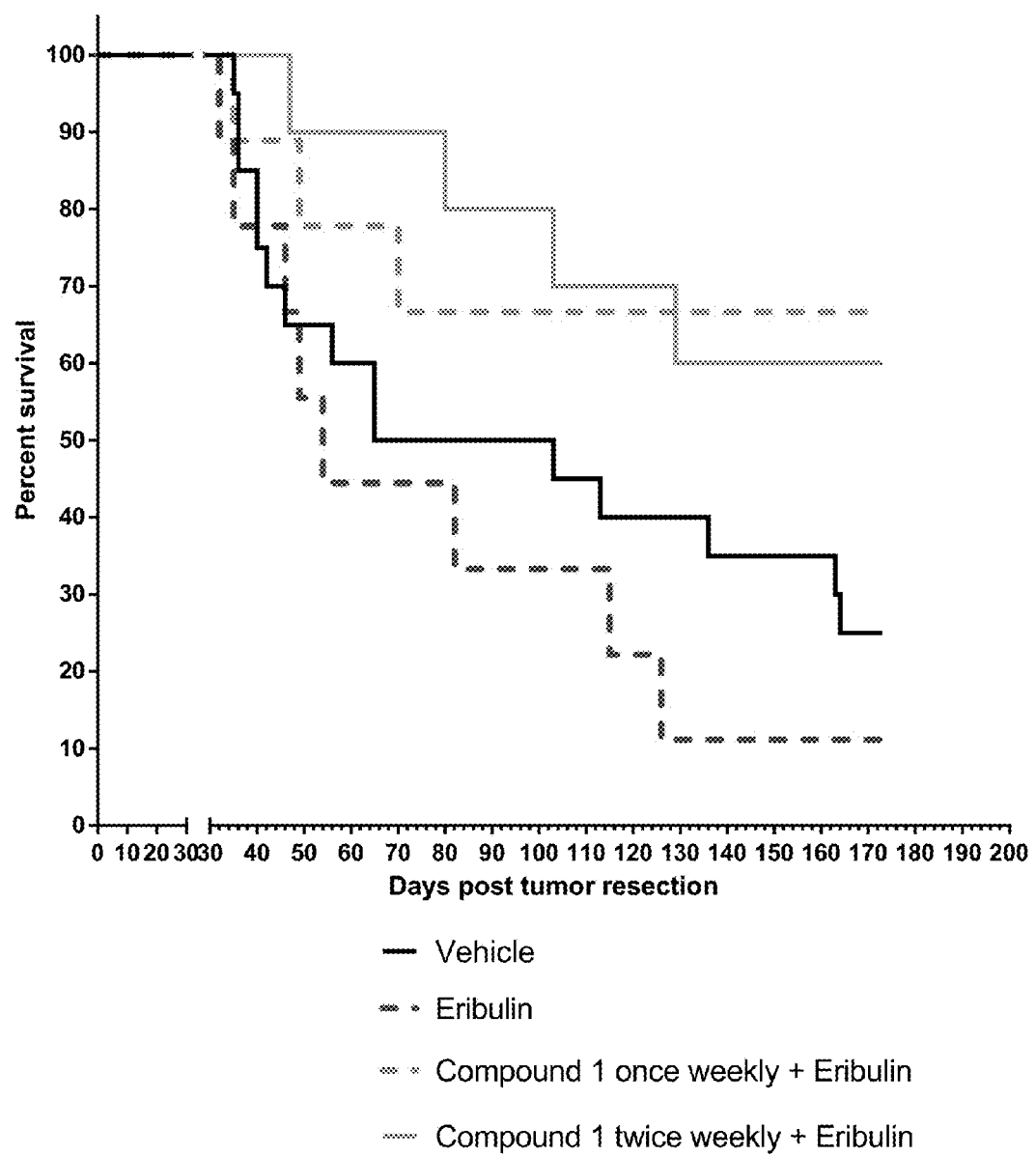
FIG. 7 shows enzymatic and in vivo activities of eribulin as a single agent or in combination with the composition of Formula II.

Increase in overall survival in the murine PyMT breast cancer model by 1-(3-tert-butyl-1-(quinolin-6-yl)-1H-pyrazol-5-yl)-3-(2-fluoro-4-(2-(methylcarbamoyl)pyridin-4-yloxy)phenyl)urea dosed intermittently (non-daily) in combination with eribulin PyMT Syngeneic Breast Cancer Model Survival Evaluation The PyMT syngeneic breast cancer implant mouse model was used to evaluate in vivo activity of compound 1. Briefly, $1 \times 10^6$ cells (dissociated from PyMT tumor fragments and stored frozen in cell-freezing medium) in 0.1 mL total volume were implanted into the fourth mammary fat pad on the left side of female mice (FVB/NJ, JAXWEST:RB05 mice from Jackson Labs). A total of ten mice were implanted in each group. Molecular Imaging, Inc.'s Animal Care and Use Committee approved all the experimental protocols and conducted experiments in compliance with all the laws, regulations and guidelines of the National Institutes of Health (NIH). Treatment was initiated by oral administration (gavage) of Compound 1 once or twice weekly or vehicle (0.4% hydroxypropylmethylcellulose in water) and/or intravenous administration (IV) of eribulin three times weekly or vehicle (80% saline) according to individual body weight on the day of treatment at 0.2 mL per 20 g when tumor size reached approximately 850 mg. Tumors were then resected three days after treatment began. Animals were then dosed for the duration of the survival experiment. Body weights and tumor measurements were recorded three times weekly. In the PyMT model, eribulin at 0.1 mg/kg evidenced no increase in survival. Compound 1 in combination with eribulin demonstrated significant increases in survival (FIG. 7). These data evidence in vivo activity by Compound 1 and show correlation to enzymatic and cell data.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of blocking breast tumor growth, invasiveness, dissemination, metastasis, or increasing survival in breast cancer in patients comprising administering to a patient whose tumor microenvironment expresses TIE2 kinase in TIE2-expressing macrophages, an effective amount of a composition of Formula I

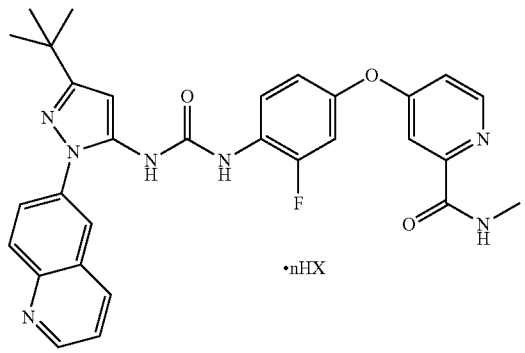

Formula I

·nHX wherein
n is an integer from 0 to 7;
X is the basic radical of a pharmaceutically acceptable salt;
provided that when n is 0, the composition of Formula I is the parent free base;
in a dosing regimen sufficient to block TIE2 kinase in tumor microenvironment TIE2-expressing macrophages.

2. The method of claim 1, wherein the dosing regimen is administered daily.

3. The method of claim 1, wherein the dosing regimen is intermittent non-daily dosing, alternate daily dosing, every third daily dosing, twice weekly dosing, or once weekly dosing.

4. The method of claim 1, wherein the composition of Formula I is used in combination with one or more agents taken from an anti-tubulin agent or an immunomodulatory agent.

5. The method of claim 1, wherein the composition of Formula I is used in combination with paclitaxel.

6. The method of claim 1, wherein the composition of Formula I is used in combination with paclitaxel protein-bound particles for injectable suspension.

7. The method of claim 1, wherein the compound of Formula I is used in combination with eribulin.

8. A method of blocking breast cancer immunotolerance, comprising administering to a patient whose tumor microenvironment expresses TIE2 kinase in TIE2-expressing macrophages, an effective amount of a composition of Formula I

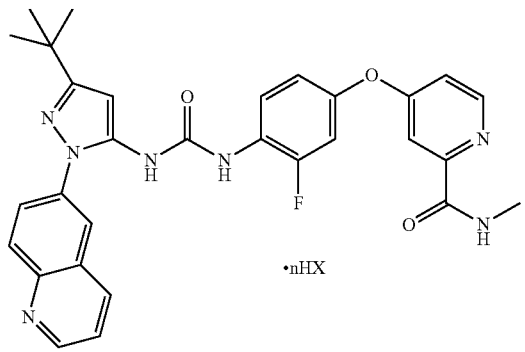

Formula I wherein
n is an integer from 0 to 7;
X is the basic radical of a pharmaceutically acceptable salt;
provided that when n is 0, the composition of Formula I is the parent free base,
in a dosing regimen sufficient to block TIE2 kinase in tumor microenvironment TIE2-expressing macrophages that mediate immunotolerance.

9. The method of claim 8, wherein the dosing regimen is administered daily.

10. The method of claim 8, wherein the dosing regimen is intermittent non-daily dosing, alternate daily dosing, every third daily dosing, twice weekly dosing, or once weekly dosing.

11. The method of claim 8, wherein the composition of Formula I is used in combination with one or more agents taken from an anti-tubulin agent or an immunomodulatory agent.

12. The method of claim 8, wherein the composition of Formula I is used in combination with paclitaxel.

13. The method of claim 8, wherein the composition of Formula I is used in combination with paclitaxel protein-bound particles for injectable suspension.

14. The method of claim 8, wherein the composition of Formula I is used in combination with eribulin.

15. The method of claim 8, wherein the composition of Formula I is used in combination with an anti-CTLA-4 agent.

16. The method of claim 8, wherein the composition of Formula I is used in combination with ipilimumab.

17. The method of claim 8, wherein the composition of Formula I is used in combination with an anti-PD-1 agent.

18. The method of claim 8, wherein the composition of Formula I is used in combination with lambrolizumab.

19. The method of claim 8, wherein the composition of Formula I is used in combination with an anti-PD L-1 agent.

20. The method of claim 8, wherein the composition of Formula I is used in combination with MPDL3280A.

21. A method of treating breast cancer patients in a neoadjuvant setting prior to surgical resection of tumor, comprising administering to a patient whose tumor microenvironment expresses TIE2 kinase in TIE2-expressing macrophages, an effective amount of the composition of Formula I

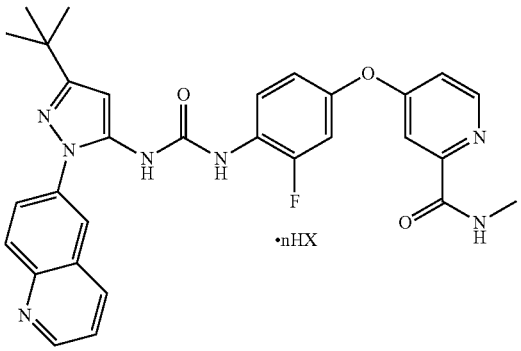

Formula I wherein
n is an integer from 0 to 7;
X is the basic radical of a pharmaceutically acceptable salt;
provided that when n is 0, the composition of Formula I is the parent free base,
prior to surgical resection of tumor in a dosing regimen sufficient to block TIE2 kinase in tumor microenvironment TIE2-expressing macrophages.

22. The method of claim 21, wherein the dosing regimen is administered daily.

23. The method of claim 21, wherein the dosing regimen is intermittent non-daily dosing, alternate daily dosing, every third daily dosing, twice weekly dosing, or once weekly dosing.

24. The method of claim 21, wherein the composition of Formula I is used in combination with paclitaxel.

25. The method of claim 21, wherein the composition of Formula I is used in combination with paclitaxel protein-bound particles for injectable suspension.

26. The method of claim 21, wherein the composition of Formula I is used in combination with eribulin.

27. The method of claim 21, wherein the composition of Formula I is used in combination with an anti-CTLA-4 agent.

28. The method of claim 21, wherein the composition of Formula I is used in combination with ipilimumab.

29. The method of claim 21, wherein the composition of Formula I is used in combination with an anti-PD-1 agent.

30. The method of claim 21, wherein the composition of Formula I is used in combination with lambrolizumab.

31. The method of claim 21, wherein the composition of Formula I is used in combination with an anti-PD L-1 agent.

32. The method of claim 21, wherein the composition of Formula I is used in combination with MPDL3280A.

33. A method of treating cancer, comprising administering to a patient whose tumors express tunica interna endothelial cell kinase-2 (TIE2 kinase), an effective amount of a composition of Formula I:

Formula I

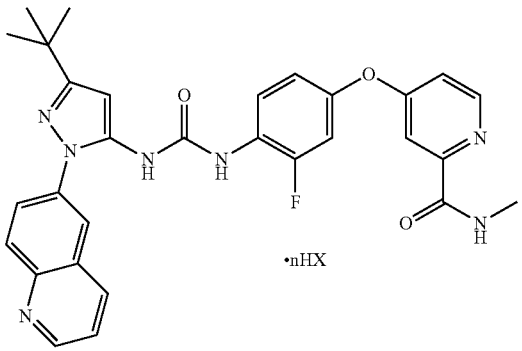

·nHX wherein
n is an integer from 0 to 7;
X is the basic radical of a pharmaceutically acceptable salt;
provided that when n is 0, the composition of Formula I is the parent free base,
wherein the patient expresses tunica interna endothelial cell kinase-2 (TIE2 kinase).

34. The method of claim 33, wherein the composition of Formula I is administered in combination with one or more other agents.

35. The method of claim 33, wherein the composition of Formula I is administered daily.

36. The method of claim 33, wherein the composition of Formula I is administered intermittent non-daily.

37. The method of claim 33, wherein the treatment comprises reducing one or more of primary tumor growth, tumor invasiveness, cancer intravasation, cancer dissemination, metastasis, and tumor immunotolerance.

38. The method of claim 34, wherein the other agent is one or more of paclitaxel, paclitaxel protein-bound particles for injectable suspension, eribulin, docetaxel, ixabepilone, vincristine, vinorelbine, cisplatin, carboplatin, oxaliplatin, cyclophosphamide, ifosfamide, temozolomide, doxorubicin, pegylated liposomal doxorubicin, daunorubicin, idarubicin, epirubicin, 5-fluorouracil, capecitabine, cytarabine, decitabine, 5-azacytadine, gemcitabine, methotrexate, erlotinib, gefitinib, lapatinib, everolimus, temsirolimus, LY2835219, LEE011, PD 0332991, crizotinib, cabozantinib, sunitinib, pazopanib, sorafenib, regorafenib, axitinib, dasatinib, imatinib, nilotinib, vemurafenib, dabrafenib, trametinib, idelasib, quizartinib, tamoxifen, fulvestrant, anastrozole, letrozole, exemestane, abiraterone acetate, enzalutamide, nilutamide, bicalutamide, flutamide, cyproterone acetate, prednisone, dexamethasone, irinotecan, camptothecin, topotecan, etoposide, etoposide phosphate, mitoxantrone, vorinostat, romidepsin, panobinostat, valproic acid, belinostat, DZNep 5-aza-2'-deoxycytidine, bortezomib, carfilzomib, thalidomide, lenalidomide, pomalidomide, trastuzumab, pertuzumab, cetuximab, panitumumab, ipilimumab, labrolizumab, nivolumab, MPDL3280A, bevacizumab, aflibercept, brentuximab vedotin, ado-trastuzumab emtansine, radiotherapy, and sipuleucel T.

39. The method of claim 34, wherein the other agent is one or more of paclitaxel, paclitaxel protein-bound particles for injectable suspension, eribulin, docetaxel, ipilimumab, labrolizumab, nivolumab, and MPDL3280A.

40. The method of claim 8, wherein the composition of Formula I is used in combination with nivolumab.

41. The method of claim 21, wherein the composition of Formula I is used in combination with nivolumab.

42. The method of claim 33, wherein the cancer is selected from breast cancer, colorectal cancer, hepatocellular carcinoma, head and neck cancer, bladder cancer, ovarian cancer, gliomas, angiosarcomas, melanomas, or acute myeloid leukemia.

* * * * *

SEQUENCE LISTING

```
<160> NUMBER OF SEQ ID NOS: 2

<210> SEQ ID NO 1
<211> LENGTH: 354
<212> TYPE: PRT
<213> ORGANISM: Homo sapiens

<400> SEQUENCE: 1

Gln Leu Lys Arg Ala Asn Val Gln Arg Arg Met Ala Gln Ala Phe Gln
1               5                   10                  15
```

```
Asn Val Arg Glu Glu Pro Ala Val Gln Phe Asn Ser Gly Thr Leu Ala
            20                  25                  30

Leu Asn Arg Lys Val Lys Asn Pro Asp Pro Thr Ile Tyr Pro Val
        35                  40                  45

Leu Asp Trp Asn Asp Ile Lys Phe Gln Asp Val Ile Gly Glu Gly Asn
 50                  55                  60

Phe Gly Gln Val Leu Lys Ala Arg Ile Lys Lys Asp Gly Leu Arg Met
 65                  70                  75                  80

Asp Ala Ala Ile Lys Arg Met Lys Glu Tyr Ala Ser Lys Asp Asp His
                 85                  90                  95

Arg Asp Phe Ala Gly Glu Leu Glu Val Leu Cys Lys Leu Gly His His
            100                 105                 110

Pro Asn Ile Ile Asn Leu Leu Gly Ala Cys Glu His Arg Gly Tyr Leu
            115                 120                 125

Tyr Leu Ala Ile Glu Tyr Ala Pro His Gly Asn Leu Leu Asp Phe Leu
130                 135                 140

Arg Lys Ser Arg Val Leu Glu Thr Asp Pro Ala Phe Ala Ile Ala Asn
145                 150                 155                 160

Ser Thr Ala Ser Thr Leu Ser Ser Gln Gln Leu Leu His Phe Ala Ala
                165                 170                 175

Asp Val Ala Arg Gly Met Asp Tyr Leu Ser Gln Lys Gln Phe Ile His
            180                 185                 190

Arg Asp Leu Ala Ala Arg Asn Ile Leu Val Gly Glu Asn Tyr Val Ala
        195                 200                 205

Lys Ile Ala Asp Phe Gly Leu Ser Arg Gly Gln Glu Val Tyr Val Lys
    210                 215                 220

Lys Thr Met Gly Arg Leu Pro Val Arg Trp Met Ala Ile Glu Ser Leu
225                 230                 235                 240

Asn Tyr Ser Val Tyr Thr Thr Asn Ser Asp Val Trp Ser Tyr Gly Val
                245                 250                 255

Leu Leu Trp Glu Ile Val Ser Leu Gly Gly Thr Pro Tyr Cys Gly Met
            260                 265                 270

Thr Cys Ala Glu Leu Tyr Glu Lys Leu Pro Gln Gly Tyr Arg Leu Glu
        275                 280                 285

Lys Pro Leu Asn Cys Asp Asp Glu Val Tyr Asp Leu Met Arg Gln Cys
    290                 295                 300

Trp Arg Glu Lys Pro Tyr Glu Arg Pro Ser Phe Ala Gln Ile Leu Val
305                 310                 315                 320

Ser Leu Asn Arg Met Leu Glu Glu Arg Lys Thr Tyr Val Asn Thr Thr
                325                 330                 335

Leu Tyr Glu Lys Phe Thr Tyr Ala Gly Ile Asp Cys Ser Ala Glu Glu
            340                 345                 350

Ala Ala

<210> SEQ ID NO 2
<211> LENGTH: 285
<212> TYPE: PRT
<213> ORGANISM: Homo sapiens

<400> SEQUENCE: 2

Pro Val Leu Asp Trp Asn Asp Ile Lys Phe Gln Asp Val Ile Gly Glu
1               5                   10                  15

Gly Asn Phe Gly Gln Val Leu Lys Ala Arg Ile Lys Lys Asp Gly Leu
            20                  25                  30
```

```
Arg Met Asp Ala Ala Ile Lys Arg Met Lys Glu Tyr Ala Ser Lys Asp
        35                  40                  45

Asp His Arg Asp Phe Ala Gly Glu Leu Glu Val Leu Cys Lys Leu Gly
    50                  55                  60

His His Pro Asn Ile Ile Asn Leu Leu Gly Ala Cys Glu His Arg Gly
65                  70                  75                  80

Tyr Leu Tyr Leu Ala Ile Glu Tyr Ala Pro His Gly Asn Leu Leu Asp
            85                  90                  95

Phe Leu Arg Lys Ser Arg Val Leu Glu Thr Asp Pro Ala Phe Ala Ile
            100                 105                 110

Ala Asn Ser Thr Ala Ser Thr Leu Ser Ser Gln Gln Leu Leu His Phe
            115                 120                 125

Ala Ala Asp Val Ala Arg Gly Met Asp Tyr Leu Ser Gln Lys Gln Phe
            130                 135                 140

Ile His Arg Asp Leu Ala Ala Arg Asn Ile Leu Val Gly Glu Asn Tyr
145                 150                 155                 160

Val Ala Lys Ile Ala Asp Phe Gly Leu Ser Arg Gly Gln Glu Val Tyr
                165                 170                 175

Val Lys Lys Thr Met Gly Arg Leu Pro Val Arg Trp Met Ala Ile Glu
            180                 185                 190

Ser Leu Asn Tyr Ser Val Tyr Thr Thr Asn Ser Asp Val Trp Ser Tyr
            195                 200                 205

Gly Val Leu Leu Trp Glu Ile Val Ser Leu Gly Gly Thr Pro Tyr Cys
    210                 215                 220

Gly Met Thr Cys Ala Glu Leu Tyr Glu Lys Leu Pro Gln Gly Tyr Arg
225                 230                 235                 240

Leu Glu Lys Pro Leu Asn Cys Asp Asp Glu Val Tyr Asp Leu Met Arg
                245                 250                 255

Gln Cys Trp Arg Glu Lys Pro Tyr Glu Arg Pro Ser Phe Ala Gln Ile
            260                 265                 270

Leu Val Ser Leu Asn Arg Met Leu Glu Glu Arg Lys Thr
    275                 280                 285
```